(12) United States Patent
Sun et al.

(10) Patent No.: US 11,701,031 B2
(45) Date of Patent: Jul. 18, 2023

(54) MOLECULARLY-IMPRINTED ELECTROCHEMICAL SENSORS

(71) Applicant: Northeastern University, Boston, MA (US)

(72) Inventors: Nian Xiang Sun, Winchester, MA (US); Shadi Emam, Boston, MA (US); Adam Keith Ekenseair, Waltham, MA (US)

(73) Assignee: Northeastern University, Boston, MA (US)

( * ) Notice: Subject to any disclaimer, the term of this patent is extended or adjusted under 35 U.S.C. 154(b) by 58 days.

(21) Appl. No.: 17/453,941

(22) Filed: Nov. 8, 2021

(65) Prior Publication Data

US 2022/0167873 A1    Jun. 2, 2022

Related U.S. Application Data

(63) Continuation of application No. 16/383,220, filed on Apr. 12, 2019, now Pat. No. 11,219,387.
(Continued)

(51) Int. Cl.
*A61B 5/097* (2006.01)
*A61B 5/08* (2006.01)
(Continued)

(52) U.S. Cl.
CPC .............. *A61B 5/097* (2013.01); *A61B 5/082* (2013.01); *G01N 27/04* (2013.01);
(Continued)

(58) Field of Classification Search
CPC ........ A61B 5/097; A61B 5/082; G01N 27/04; B32B 9/041; B32B 15/08
See application file for complete search history.

(56) References Cited

U.S. PATENT DOCUMENTS 6,004,442 A    12/1999   Choulga et al.
2016/0377611 A1   12/2016   Ma et al.

FOREIGN PATENT DOCUMENTS

WO    WO2010/025547 A1    3/2010
WO    WO2013/022545 A1    2/2013

OTHER PUBLICATIONS

2018 Alzheimer's disease facts and figures, Alzheimer's association, (2018), 1-88.
(Continued)

*Primary Examiner* — Jennifer Wecker
*Assistant Examiner* — Kathryn Elizabeth Limbaugh
(74) *Attorney, Agent, or Firm* — Hamilton, Brook, Smith & Reynolds, P.C.

(57) ABSTRACT

Provided herein are devices (e.g., electrochemical sensors useful for detecting volatile organic compounds associated with certain diseases or conditions and/or diagnosing certain diseases or conditions). The devices comprise one or more layers of metal on a layer of silicon, and a layer of molecularly imprinted polymer in electrical communication with the one or more layers of metal, wherein the one or more layers of metal are each independently selected from a layer of chromium, platinum, gold, nickel, cobalt, tungsten, rhodium, iridium, silver, tin, titanium or tantalum, or an alloy thereof. Methods of using the devices (e.g., to detect one or more analytes in a sample, to detect and/or diagnose a disease or condition in a subject), and methods of making the devices are also provided.

19 Claims, 26 Drawing Sheets

Related U.S. Application Data

(60) Provisional application No. 62/657,312, filed on Apr. 13, 2018.

(51) Int. Cl.
    *G01N 27/04*         (2006.01)
    *G01N 27/327*      (2006.01)
    *B32B 9/04*         (2006.01)
    *B32B 15/08*       (2006.01)

(52) U.S. Cl.
    CPC .......... *G01N 27/3275* (2013.01); *B32B 9/041* (2013.01); *B32B 15/08* (2013.01); *G01N 2800/2821* (2013.01)

(56) References Cited

OTHER PUBLICATIONS

Algieri, C., et al., "Bio-Mimetic Sensors Based on Molecularly Imprinted Membranes", Sensors, 2014, 14 13863-13912.
Alizadeh, T. et al., "Graphene/graphite/molecularly imprinted polymer nanocomposite as the highly selective gas sensor for nitrobenzene vapor recognition", Journal of Environmental Chemical Engineering 2014, 2, 1514-1526.
Alzheimer's Association, 2016 Alzheimer's disease facts and figures, *Alzheimer's & Dementia 2016*, 12, 459-509.
Bach, J., et al., "Measuring Compounds in Exhaled Air to Detect Alzheimer's Disease and Parkinson's Disease", PLOS One, 13 pgs, (Jul. 13, 2015).
Bredesen, D.E., et al., "Reversal of cognitive decline: A novel therapeutic program", Aging 6(9): 707-717 (Sep. 2014).
Broza, Y., et al., "Nanomaterial-based sensors for detection of disease by volatile organic compounds", Nanomedicine (2013) 8(5): 785-806.
Buszewski, B., et al., "Human exhaled air analytics: biomarkers of diseases", Biomedical Chromatography, 21: 553-566 (2007).
Canter, R. G., et al., "The road to restoring neutral circuits for the treatment of Alzheimer's disease", Nature 2016, 539.
Capuano, R., et al., "The lung cancer breath signature: a comparative analysis of exhaled breath and air sampled from inside the lungs", Scientific Reports, 5:16491, 10 pages (2015).
Chen, X., et al., "A study of an electronic nose for detection of lung cancer based on a virtual SAW gas sensors array and imaging recognition method", Meas. Sci. Technol. 16 (2005) 1535-1546.
Chen, X., et al., "Molecular imprinting: perspectives and applications" Chem. Soc. Rev., 2016, 45, 2137.
Cui, M., et al., "A Molecularly-Imprinted Electrochemical Sensor Based on a Graphene-Prussian blue Composite-Modified Glassy Carbon Electrode for the Detection of Butylated Hydroxyanisole in Foodstuffs", 2013, J. Analyst 138: 5949-5955.
De Meyer, G., et al., "Diagnosis-Independent Alzheimer Disease Biomarker Signature in Cognitively Normal Elderly People", Arc Neurol, 67(8): 949-956 (Aug. 2010).
Dekansi, A., et al., "Glassy carbon electrodes Characterization and electrochemical activation", Carbon 39 (2001) 1195-1205.
Dent, A.G., et al., "Exhaled breath analysis for lung cancer", J. Thorac Dis 2013; 5(S5): S540-S550.
Dickert, F.L., et al., "Synthetic receptors for chemical sensors-subnano- and micrometer patterning by imprinting techniques", J of Biosensors and Bioelectronics, 2004, 20(6), 1040-1044.
Dumurgier, J., et al., "Alzheimer's Biomarkers and Future Decline in Cognitive Normal Older Adults", J. Alzheimers Dis. 2017; 60(4): 1451-1459.
Emam, S., et al., "A Molecularly-Imprinted Electrochemical Gas Sensor to Detect Pivalic Acid in the Air," RISE:2018 Research, Innovation & Scholarship Expo, Northeastern University, Apr. 5, 2018.
Emam, S., et al., "A Molecularly-Imprinted Electrochemical Gas Sensor to Sense Butylated Hydroxytoluene in Air", 2018, J of Sensors 2018: 1-9.
Emam, S., et al., "Electrochemical Gas Sensor to Diagnose Alzheimer's Disease Through Exhaled Breath," RISE:2017 Research, Innovation & Scholarship Expo, Northeastern University, Apr. 13, 2017.
Ertürk, G., et al., "Molecular imprinting techniques used for the preparation of biosensors", Sensors, 2017, 17, 288.
Gan, et al: "Electrochemical sensors based on graphene materials", Microchimica Acta ; An International Journal On Micro And Traceanalysis, Springer-Verlag, VI, vol. 175, No. 1-2, Jul. 7, 2011.
Gunther, E.C., et al., "Rescue of Transgenic Alzheimer's Pathophysiology by Polymeric Cellular Prion Protein Antagonists", Cell Reports 26, 145-158, Jan. 2, 2019.
Hibbard, T., et al., Breath ammonia analysis: Clinical application and measurement. Breath Ammon. Clin. App. Meas. 2011, 41, 21-35.
Hu, W.T., et al., "Biomarker Discovery of Alzheimer's Disease, Frontotemporal Lobar Degeneration and Parkinson's Disease", Acta Neuropathol. Sep. 2010; 120(3): 385-399.
Hummers W. S., et al., "Preparation of graphene oxide", J. Am. Chem. Soc. 1958, 80, 1339.
Hwang, EH., et al., "Transport in chemically doped graphene in the presence of adsorbed molecules". Phys. Rev. B 76:195-421 (Oct. 30, 2018).
Iaccarino F.H. et al., "Gamma frequency entrainment attenuates amyloid load and modifies microglia" *Nature* 2016, 540, 230-252.
Janiak, D.S., et al., "Molecular imprinting of peptides and proteins in aqueous media", Anal Bioanal Chem 2007, 389, 399-404.
Jin, E., et al., "Fabrication of graphene/prussian blue composite nanosheets and their electrocatalytic reduction of $H_2O_2$", Electrochimica Acta 2010, 55, 7230-7234.
Katsnelson, M.I., et al., "Graphene: new bridge between condensed matter physics and quantum electrodynamic," (2007) J of Solid State Commun. 143: 3-13.
Kleisiaris, C.F., et al., "Health care practices in ancient Greece: The Hippocratic ideal", J Med Ethics Hist Med, 7 (6): 1-5 (2014).
Li, J, et al., "Prussian Blue/Reduced Graphene Oxide Composite for the Amperometric Determination of Dopamine and Hydrogen Peroxide", Analytical Letters 2015, 48:17, 2786-2798, DOI: 10.1080/00032719.2015.1052141.
Li, X., et al., "Highly sensitive protein molecularly imprinted electro-chemical sensor based on bold microdendrites electrode and Prussian blue mediated amplification", Biosensors and Bioelectronics 42 (2013): 612-617.
Liguoril, C., et al., "Beta-amyloid and phosphorylated tau metabolism changes in narcolepsy over time", Sleep Breath 2016, 20, 277-283.
Lin, CY., et al., "Discrimination of Peptides by Using a Molecularly Imprinted Piezoelectric Biosensor" Chem. Eur. J. 2003, 9: 5107-5110.
Mazzatenta, A., et al., "Volatile organic compounds (VOCs) fingerprint of Alzheimer's disease", *Respiratory Physiology & Neurobiology* 2015, 209, 81-84.
McKhann, G.M., et al., "The diagnosis of dementia due to Alzheimer's disease: recommendations from the National Institute on Aging-Alzheimer's Association workgroups on diagnostic guidelines for Alzheimer's disease", Alzheimer's & Dementia, 7 (2011) 263-269.
Michaelson, D.M., (2014). "APOE epsilon4: the most prevalent yet understudied risk factor for Alzheimer's disease" Alzheimers Dement, 10(6): 861-868.
Nakamura, A., et al., "High performance plasma amyloid-β biomarkers for Alzheimer's disease", 2018, Nature 554: 249-273.
Nakhleh, M.K., et al. , "Diagnosis and classification of 17 diseases from 1404 subjects via pattern analysis of exhaled molecules", ACS Nano 2017, 11, 112-125.
Non-Final Office Action for U.S. Appl. No. 16/383,220, "Molecularly-Imprinted Electrochemical Sensors" dated May 4, 2021.
Notice of Allowance for U.S. Appl. No. 16/383,220, "Molecularly-Imprinted Electrochemical Sensors", dated Sep. 1, 2021.
Notification of Transmittal of the International Search Report and the Written Opinion of the International Searching Authority, or the Declaration for PCT/US2021/014248, entitled "Devices and Methods for Detection of Viruses from Exhaled Breath", dated Apr. 28, 2021.

(56) References Cited

OTHER PUBLICATIONS

Park, S., et al., "Hydrazine-reduction of graphite- and graphene oxide" Carbon 2011, 49, 3019-3023.

Pauling, L., et al., "Quantitative analysis of urine vapor and breath by gas-liquid partition chromatography", Proc Natl Acad Sci, 68 (10):2374-6 (Oct. 1971).

Pei, S., et al., "The reduction of graphene oxide", Carbon, 50 (2012) 3210-3228.

Peng, G., et al., "Detection of Nonpolar Molecules by Means of Carrier Scattering in Random Networks of Carbon Nanotubes: Toward Diagnosis of Diseases via Breath Samples", Nanoletters, 9(4): 1362-1368 (Jan. 2009).

Ping, A., et al., "An amperometric sensor based on Prussian blue and poly(o-phenylenediamine) modified glassy carbon electrode for the determination of hydrogen peroxide in beverages", Food Chem. 2011, 126, 2005-2009.

Rajesh, et al: "Single Frequency Impedance Analysis on Reduced Graphene Oxide Screen-Printed Electrode for Biomolecular Detection", Applied Biochemistry And Biotechnology, Humana Press Inc, New York, vol. 183, No. 2, May 22, 2017.

Rebelo, et al: "Molecularly imprinted polymer SPE sensor for analysis of CA-125 on serum", Analytica Chimica Acta, Elsevier, Amsterdam, Nl, vol. 1082, Jul. 26, 2019.

Saylan, Y., et al., "Molecular Imprinting of Macromolecules for Sensor Applications," *Sensors*, 2017, 17, 898.

Schedin, F., et al., "Detection of individual gas molecules adsorbed on graphene", Nat. Mater. 2007, 6, 652-655, doi:http://dx.doi.org/10.1038/nmat1967. 17660825.

Schmidt, F.M., et al., "Ammonia in breath and emitted from skin". *J. Breath Res*. 2013, 7, 017109.

Sharma, et al: "Surface Plasmon Resonance Based Highly Selective Fiber Optic Dopamine Sensor Fabricated Using Molecular Imprinted GNP/Sn02 Nanocomposite", Journal Of Lightwave Technology, IEEE, USA, vol. 36, No. 24, Dec. 15, 2018.

Selkoe, DJ., et al., "The role of APP processing and trafficking pathways in the formation of amyloid beta-protein", Ann. NY Acad. Sci. 1996, 777, 57-64.

Stankovich, S., et al., "Synthesis of graphene-based nanosheets via chemical reduction of exfoliated graphite oxide", Carbon 45 (2007) 1558-1565.

Supplemental Notice of Allowability for U.S. Appl. No. 16/383,220, "Molecularly-Imprinted Electrochemical Sensors", dated Nov. 3, 2021.

Tisch, U., et al., "Detection of Alzheimer's and Parkinson's disease from exhaled breath using nanomaterial-based sensors", 2013, J Nanomedicine 8(1): 43-56.

Urraca, et al., "Polymeric complements to the Alzheimer's disease biomarker β-amyloid isoforms Aβ1-40 and Aβ1-42 for blood serum analysis under denaturing conditions", Journal of the American chemical society 2011, 133, 9220-9223.

Van der Linden, W.E., et al., "Glassy carbon as electrode material in electro- analytical chemistry", Anal Chim Acta 1980; 119:1-24.

Vasapollo, G., et al., "Molecularly Imprinted Polymers: Present and Future Prospective", *Int. J. Mol. Sci*. 2011, 12, 5908-5945.

Yang, et al: "Immunosensor for the detection of cancer biomarker based on percolated graphene thin film", Chemical Communications, vol. 46, No. 31, Jun. 28, 2010.

Zhang, et al: "Multifunctional oligomer immobilized on quartz crystal microbalance: a facile and stabilized molecular imprinting strategy for glycoprotein detection", Analytical And Bioanalytical Chemistry, Springer Berlin Heidelberg, DE, vol. 411, No. 17, May 22, 2019.

Zhang, M., et al., "Interlocked graphene-Prussian blue hybrid composites enable multifunctional electrochemical applications", Biosensors and Bioelectronics 2017, 89, 570-577.

Zhao, J. et al., "Graphene quantum dots-based platform for the fabrication of electrochemical biosensors", Electrochem. Commun. 2011, 13, 31-33.

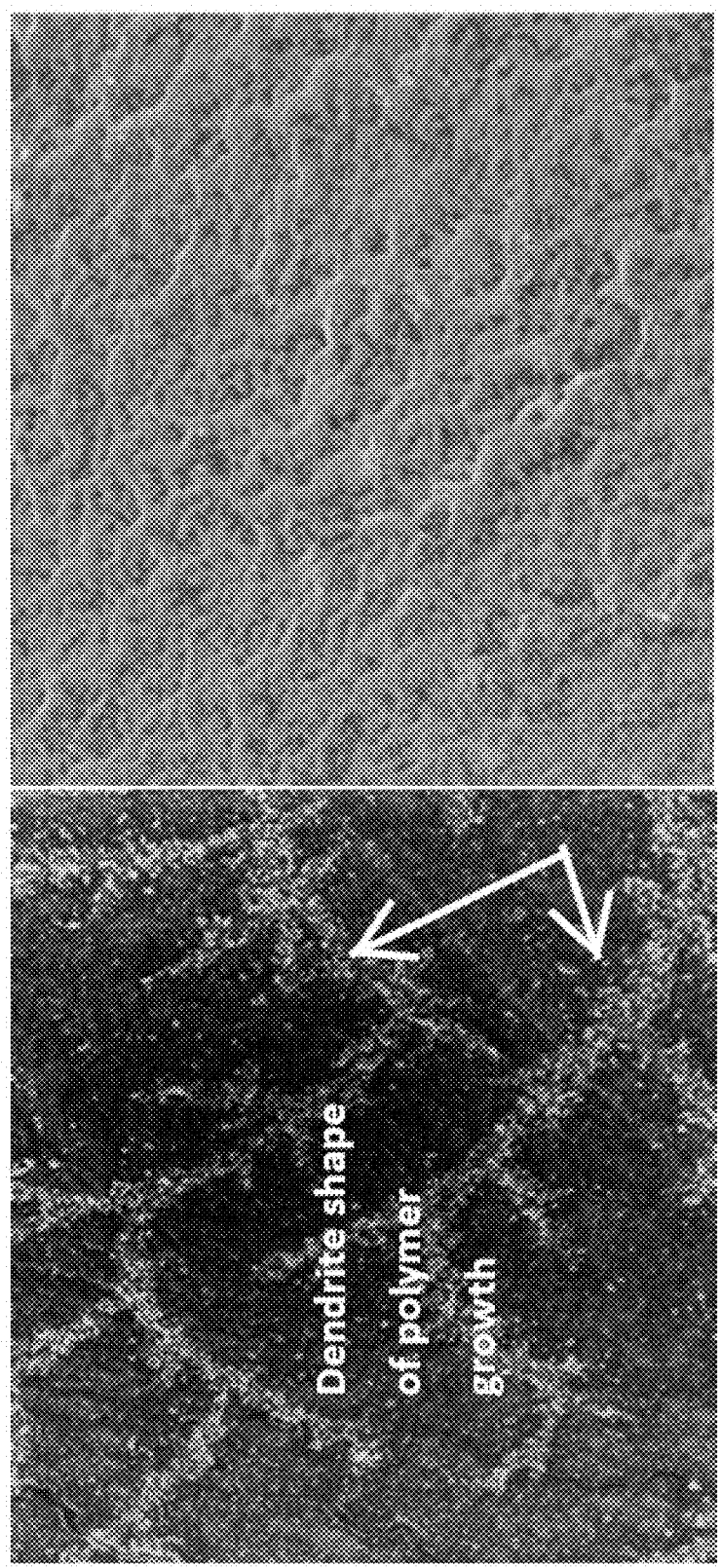

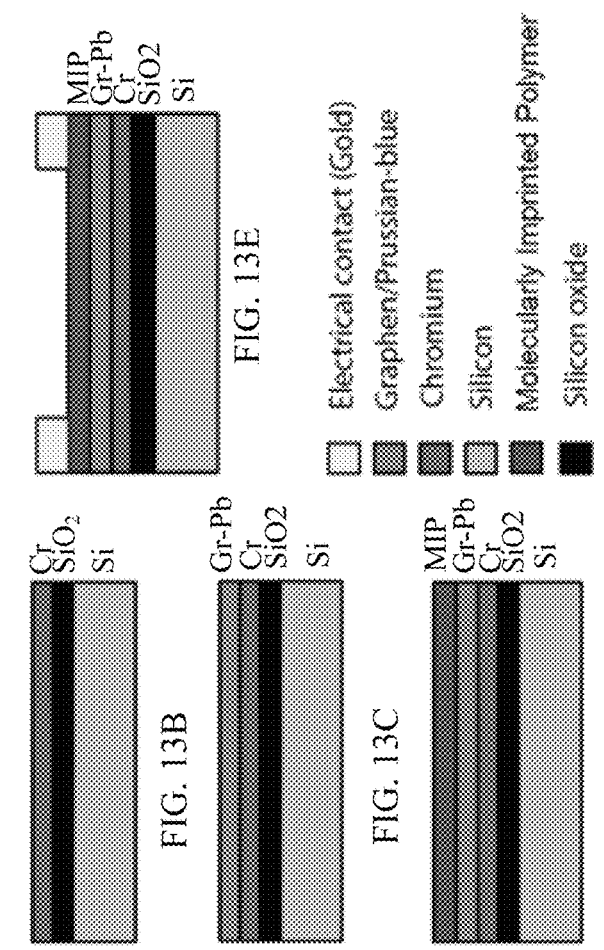
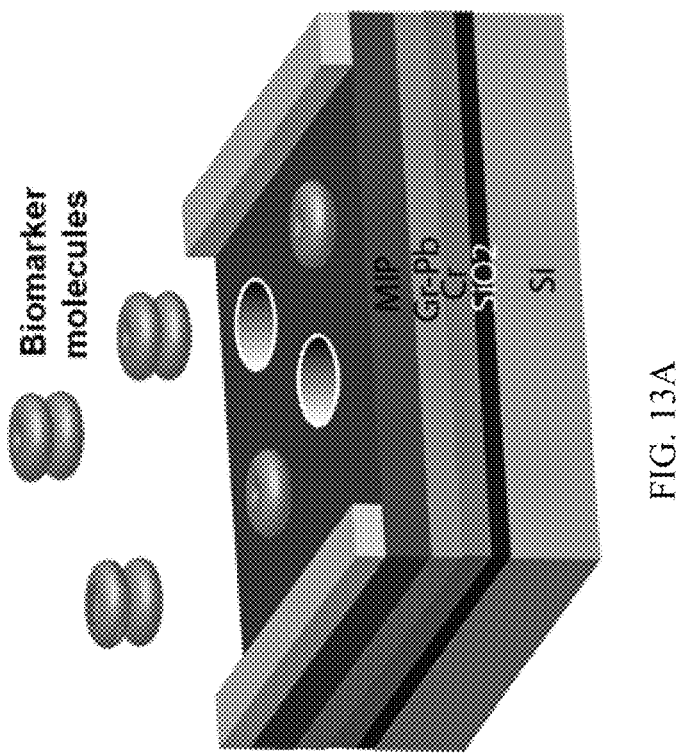
FIG. 13A
FIG. 13B
FIG. 13C
FIG. 13D
FIG. 13E

MOLECULARLY-IMPRINTED ELECTROCHEMICAL SENSORS

RELATED APPLICATIONS

This application is a continuation of U.S. application Ser. No. 16/383,220, filed on Apr. 12, 2019, which claims the benefit of U.S. Provisional Application No. 62/657,312, filed on Apr. 13, 2018. The entire teachings of these applications are incorporated herein by reference.

BACKGROUND

Alzheimer's disease (AD) is a neurodegenerative disease that affects millions of people worldwide. The diagnosis of AD is time-consuming, expensive, invasive and labor-intensive, and the procedures involved in the diagnosis of AD are particularly difficult and tedious for older patients. The sooner the disease can be diagnosed, the better treatment options are available. For example, there is evidence that dementia can be reversed if it is diagnosed at an early stage.

Exhaled breath gas analysis offers an inexpensive, non-invasive and immediate method for detecting a large number of diseases, including AD. In fact, sensors based on functionalized nanomaterials have been used to sense AD biomarkers in the breath of AD patients. However, these nanomaterial-based sensors were qualitative only, not selective and relied on pattern recognition.

Accordingly, there is a need for devices that can provide a quantitative, selective, sensitive and early detection of analytes associated with a disease, such as AD, for example, in the exhaled breath of those suspected to be afflicted with the disease.

SUMMARY

Provided herein are devices that can be used as electrochemical sensors, e.g., to selectively detect one or more analytes in a sample, such as a breath sample obtained from a subject with Alzheimer's disease (AD)p-7. Also provided herein are methods of using the devices (e.g., to detect one or more analytes in a sample, to detect and/or diagnose a disease or condition in a subject) and methods of making the devices.

One embodiment is a device, comprising one or more layers of metal (e.g., one layer of chromium) on a layer of silicon, and a layer of molecularly imprinted polymer in electrical communication with the one or more layers of metal. The one or more layers of metal are each independently selected from a layer of chromium, platinum, gold, nickel, cobalt, tungsten, rhodium, iridium, silver, tin, titanium or tantalum, or an alloy thereof.

Another embodiment is a device comprising a layer of silicon having a thickness of from about 100 microns to about 1 millimeter; a layer of chromium on the layer of silicon, the layer of chromium and the layer of silicon having a combined resistance of about 60 ohms; from about 5 to about 15 layers of graphene on the layer of chromium and in electrical communication with the layer of chromium; a layer of molecularly imprinted polypyrrole on the layers of graphene and in electrical communication with the layers of graphene; and one or more electrical contacts in electrical communication with the layer of molecularly imprinted polypyrrole. The layers of graphene comprise potassium ferrocyanide. The device is about 5 millimeters or less in length, about 5 millimeters or less in width, and about 5 millimeters or less (e.g., about 1 millimeter or less) in height; and has a resistance of from about 10 ohms to about 100 ohms.

Yet another embodiment is a system comprising a device described herein and an ohmmeter in electrical contact with the device.

Another embodiment is a method of detecting one or more analytes in a sample (e.g., a breath, sweat, blood or urine sample, especially a breath sample, from a subject). The method comprises measuring the resistance of a device described herein (e.g., a device selective for one or more analytes) that has been or is in contact with a sample. The device has an inherent resistance. A difference between the inherent resistance of the device and the resistance of the device contacted with the sample indicates the presence of at least one of the one or more analytes in the sample.

Another embodiment is a method of detecting one or more analytes associated with a disease or condition in a subject suspected to have the disease or condition, or at risk for developing the disease or condition. The method comprises measuring the resistance of a device described herein that has been or is in contact with a sample (e.g., a breath, sweat, blood or urine sample, especially a breath sample) obtained from the subject. The device has an inherent resistance, and is selective for one or more analytes associated with the disease or condition. A difference between the inherent resistance of the device and the resistance of the device contacted with the sample indicates one or more analytes associated with the disease or condition have been detected.

Another embodiment is a method of diagnosing a disease or condition in a subject suspected to have the disease or condition, or at risk for developing the disease or condition. The method comprises measuring the resistance of a device described herein that has been or is in contact with a sample (e.g., a breath, sweat, blood or urine sample, especially a breath sample) obtained from the subject. The device has an inherent resistance, and is selective for one or more analytes associated with the disease or condition. A difference between the inherent resistance of the device and the resistance of the device contacted with the sample indicates the subject has the disease or condition.

Another embodiment is a method of making a device, comprising applying one or more layers of metal to a layer of silicon; and applying a layer of molecularly imprinted polymer to the device such that the layer of molecularly imprinted polymer is in electrical communication with the one or more layers of metal. The one or more layers of metal are each independently selected from a layer of chromium, platinum, gold, nickel, cobalt, tungsten, rhodium, iridium, silver, tin, titanium or tantalum, or an alloy thereof.

The devices described herein have been demonstrated to show sensitivity of from about 20 to about 100 parts per trillion (ppt), to be highly selective, and to be capable of differentiating between transgenic human APE4 knock-in rats with AD and healthy controls.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 8A is a scanning electron microscope (SEM) image, and shows the graphene sensor of Example 1 with a dendritic shape of polymer growth.

FIG. 8B is a SEM image, and shows the graphene-Prussian blue sensor of Example 1.

FIG. 13A is a schematic of a device (e.g., a breath sensor) in an embodiment of the invention, and shows a device with a size of 5×5×1 mm$^3$.

FIG. 13B is a schematic, and shows a 20-nanometer layer of chromium deposited on an oxidized silicon substrate.

FIG. 13C is a schematic, and shows several layers of graphene-Prussian blue screen-printed on a 20-nanometer layer of chromium, which is deposited on an oxidized silicon substrate.

FIG. 13D is a schematic, and shows a layer of molecularly imprinted polymer on several layers of graphene-Prussian blue screen-printed on a 20-nanometer layer of chromium, which is deposited on an oxidized silicon substrate.

FIG. 13E is a schematic, and shows a 50-nanometer thick gold electrode deposited and patterned on a layer of molecularly imprinted polymer, which is on several layers of graphene-Prussian blue screen-printed on a 20-nanometer layer of chromium, which is, in turn, deposited on an oxidized silicon substrate.

DETAILED DESCRIPTION

Figure 1:
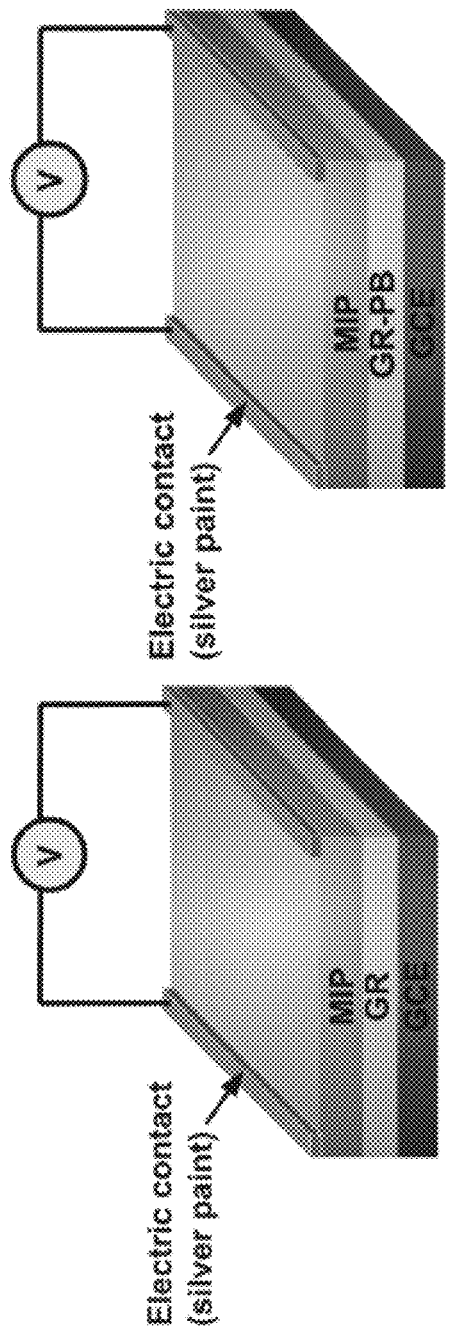
FIG. 1 is a schematic of two sensors, and shows a layer of molecularly imprinted polymer deposited on a graphene—(left sensor) or graphene-Prussian blue—(right sensor) modified surface of a glassy carbon electrode.

A description of example embodiments follows.

As used herein, the singular forms "a," "an" and "the" include plural referents unless the context clearly dictates otherwise. Thus, for example, reference to "a layer" can include a plurality of layers. Further, the plurality can comprise more than one of the same layer, or a plurality of different layers.

One embodiment is a device, comprising one or more layers of metal (e.g., 1, 2, 3, 4, 5, etc.) on a layer of silicon, and a layer of molecularly imprinted polymer in electrical communication with the one or more layers of metal. The one or more layers of metal are each independently selected from a layer of chromium, platinum, gold, nickel, cobalt, tungsten, rhodium, iridium, silver, tin, titanium or tantalum, or an alloy thereof (e.g., nickel-tungsten, nickel-chromium).

Silicon substrates, such as silicon wafers, typically form a layer of silicon dioxide upon exposure to air, or come with a layer of silicon dioxide grown thereon, e.g., using one of a variety of oxidation processes known in the art (e.g., wet or dry oxidation). "A layer of silicon," as used herein, is meant to encompass a layer of silicon including a layer of silicon dioxide. Typically, only one surface (e.g., top surface, bottom surface) of a layer of silicon includes a layer of silicon dioxide, but both surfaces (e.g., top surface and bottom surface) of a layer of silicon can include a layer of silicon dioxide. When a layer of silicon includes a layer of silicon dioxide, one or more layers of metal on the layer of silicon can be in physical contact with a silicon-containing surface. Alternatively, one or more layers of metal on a layer of silicon can be in physical contact with a silicon dioxide-containing surface, as depicted in FIG. 13A.

In some aspects, the layer of silicon dioxide is from about 1 nanometer to about 1 micron, from about 1 nanometer to about 500 nanometers, from about 1 nanometer to about 100 nanometers, from about 1 nanometer to about 50 nanometers or from about 1 nanometer to about 10 nanometers thick. In a particular aspect, the layer of silicon dioxide is about 5 nanometers thick.

Passivation refers to a material becoming passivate, that is, less affected or corroded by the environment. In an aspect, the metal, or alloy thereof, does not passivate upon exposure to air, or passivates upon exposure to air but does not develop a thick layer of oxide as a result of passivating. Metals that do not passivate upon exposure to air, or passivate upon exposure to air but do not develop a thick layer of oxide as a result of passivating include, but are not limited to, chromium, platinum, gold, nickel, cobalt, tungsten, rhodium, iridium, silver and tin. Accordingly, in some aspects, the one or more layers of metal are each independently selected from a layer of chromium, platinum, gold, nickel, cobalt, tungsten, rhodium, iridium, silver or tin, or an alloy thereof. In some aspects, the one or more layers of metal are each independently selected from chromium, nickel, cobalt, tungsten, rhodium, iridium, silver or tin, or an alloy thereof. In some aspects, the one or more layers of metal are each independently selected from chromium, or an alloy thereof.

In some aspects, the device comprises one layer of metal, and the metal is chromium, platinum, gold, nickel, cobalt, tungsten, rhodium, iridium, silver, tin, titanium or tantalum, or an alloy thereof. In a more particular aspect, the device comprises one layer of metal, and the metal is chromium, platinum, gold, nickel, cobalt, tungsten, rhodium, iridium, silver or tin, or an alloy thereof. In a yet more particular aspect, the device comprises one layer of metal, and the metal is chromium, nickel, cobalt, tungsten, rhodium, iridium, silver or tin, or an alloy thereof. In another aspect, the device comprises one layer of metal, and the metal is chromium, or an alloy thereof. In another aspect, the device comprises one layer of metal, and the metal is chromium.

In another aspect, the one or more layers of metal (e.g., one layer of chromium) is from about 5 microns to about 50 microns, from about 10 microns to about 25 microns or from about 10 microns to about 20 microns thick. In a particular aspect, the one or more layers of metal (e.g., one layer of chromium) is about 15 microns thick.

In yet another aspect, the layer of silicon is from about 50 microns to about 5 millimeters, from about 250 microns to about 1 millimeter, from about 250 microns to about 650 microns or from about 350 microns to about 400 microns thick. In some aspects, the layer of silicon is about 275 microns, about 375 microns, about 525 microns, about 625 microns, about 675 microns, about 725 microns, about 775 microns or about 925 microns thick. In a particular aspect, the layer of silicon is about 375 microns thick.

In another aspect, the one or more layers of metal (e.g., one layer of chromium) and the layer of silicon have a combined resistance of from about 1 ohm to about 1,000 ohms, from about 1 ohm to about 100 ohms, from about 10 ohms to about 100 ohms, from about 25 ohms to about 100 ohms, or from about 50 ohms to about 75 ohms. In a particular aspect, the one or more layers of metal (e.g., one layer of chromium) and the layer of silicon have a combined resistance of about 60 ohms.

In another aspect, the layer of molecularly imprinted polymer is from about 1 nanometer to about 5 millimeters, from about 1 nanometer to about 1 millimeter, from about 5 nanometers to about 500 nanometers, from about 10 nanometers to about 100 nanometers or from about 10 nanometers to about 50 nanometers thick. In a particular aspect, the layer of molecularly imprinted polymer is about 20 nanometers thick.

In another aspect, the resistance of the device is from about 1 ohm to about 1,000 ohms, from about 1 ohm to about 100 ohms, from about 10 to about 100 ohms, from about 25 ohms to about 100 ohms, or from about 50 ohms to about 75 ohms. In a particular aspect, the resistance of the device is about 60 ohms.

In another aspect, the device further comprises one or more (e.g., 1, 2, 3, 4, 5, 6, 7, 8, 10, 15, about 15, 20, about 20, 25, about 25, 50, about 50, 75, about 75, 100, about 100, 150, about 150, 200, about 200, 250, about 250, 300, about 300, 350, about 350, 400, about 400, 450, about 450, 500 or about 500) layers of graphene (e.g., reduced graphene oxide). In some aspects, the one or more layers of graphene (e.g., reduced graphene oxide) are between the layer of metal and the layer of molecularly imprinted polymer, the one or more layers of graphene being in electrical communication with the one or more layers of metal and the layer of molecularly imprinted polymer. Accordingly, another embodiment is a device comprising one or more layers of metal (e.g., one layer of metal) on a layer of silicon; one or more layers of graphene (e.g., one or more layers of reduced graphene oxide) on the one or more layers of metal; and a layer of molecularly imprinted polymer on the one or more layers of graphene. The one or more layers of graphene are in electrical communication with the one or more layers of metal and the layer of molecularly imprinted polymer.

As used herein, "graphene" refers to a single-layer sheet of $sp^2$-bonded carbon atoms arranged in a hexagonal, honeycomb lattice. Graphene typically contains defects, such as oxygen- or nitrogen-centered defects. "Graphene" is meant to encompass these species as well. Thus, as used herein, "graphene" includes graphene oxide (GO) and reduced graphene oxide (rGO, GR).

"Graphene oxide" or "GO" is graphene modified with oxygen-containing functional groups such as epoxides, carbonyls, carboxyls and alcohols. Typically, the carbon to oxygen ratio of graphene oxide is about three to about one. In some aspects, graphene is graphene oxide.

"Reduced graphene oxide," "rGO" or "GR" is the product resulting from the reduction of graphene oxide. Reduced graphene oxide can be produced by a number of techniques known in the art, including the so-called Hummer method, wherein a solution of graphene oxide is exposed to hydrazine hydrate, and the solution is maintained at about 100° C. for about 24 hours. In some aspects, graphene is reduced graphene oxide.

In some aspects, graphene (e.g., reduced graphene oxide) comprises potassium ferrocyanide (also known as Prussian blue). Methods of making graphene comprising potassium ferrocyanide are known in the art and described in the Exemplification herein.

When a device comprises one or more layers of graphene (e.g., reduced graphene oxide), the device comprises from about one to about 500, from about one to about 50, from about one to about 25, or from about 5 to about 15 layers of graphene. For example, the device comprises 1, 2, 3, 4, 5, 6, 7, 8, 10, 15, about 15, 20, about 20, 25, about 25, 50, about 50, 75, about 75, 100, about 100, 150, about 150, 200, about 200, 250, about 250, 300, about 300, 350, about 350, 400, about 400, 450, about 450, 500 or about 500 layers of graphene. In a particular aspect, the device comprises from about 5 to about 10 layers of graphene (e.g., reduced graphene oxide).

It will be understood that molecularly imprinted polymers, like polymers generally, are composed substantially or entirely of repeated monomeric subunits. Polymers can, therefore, be said to be derived from the monomers that make up the repeated monomeric subunits. For example, polypyrrole can be described as being derived from pyrrole. Examples of monomers from which a molecularly imprinted polymer can be derived include acrylic acid, methacrylic acid, 2-(trifluoromethly)acrylic acid, itaconic acid, p-vinylbenzoic acid, 2-acrylamido-2-methyl-1propansulfonic acid, divinylbenzene, 4-vinylbenzene boronic acid, 2-vinylpyridine, 4-vinylpyridine, N,N-diethylaminoethylmethacrylate, 1-vinylimidazole, allylamine, 4-(5-vinylimidazole), N-(2-aminoethyl)methacrylamide, N,N'-diethyl-4-styrylamidine, N,N,N-trimethylaminoethylmethacrylate, N-vinylpyrrolidone, urocanic ethyl ester, pyrrole, methyl methacrylate, 2-hydroxyethylmethacrylate, 4-ethyl styrene, acrylamide, methacrylamide, trans-3-(3-pyridyl)-acrylic acid, acrylonitrile and styrene, and any combination of the foregoing. In some aspects, the molecularly imprinted polymer is derived from acrylic acid, methacrylic acid, 2-(trifluoromethly) acrylic acid, itaconic acid, p-vinylbenzoic acid, 2-acrylamido-2-methyl-1propansulfonic acid, divinylbenzene, 4-vinylbenzene boronic acid, 2-vinylpyridine, 4-vinylpyridine, N,N-diethylaminoethylmethacrylate, 1-vinylimidazole, allylamine, 4-(5-vinylimidazole), N-(2-aminoethyl) methacrylamide, N,N'-diethyl-4-styrylamidine, N,N,N-trimethylaminoethylmethacrylate, N-vinylpyrrolidone, urocanic ethyl ester, pyrrole, methyl methacrylate, 2-hydroxyethylmethacrylate, 4-ethyl styrene, acrylamide, methacrylamide, trans-3-(3-pyridyl)-acrylic acid, acrylonitrile or styrene, or a combination of any of the foregoing. In a particular aspect, the molecularly imprinted polymer is derived from pyrrole.

Figure 2:
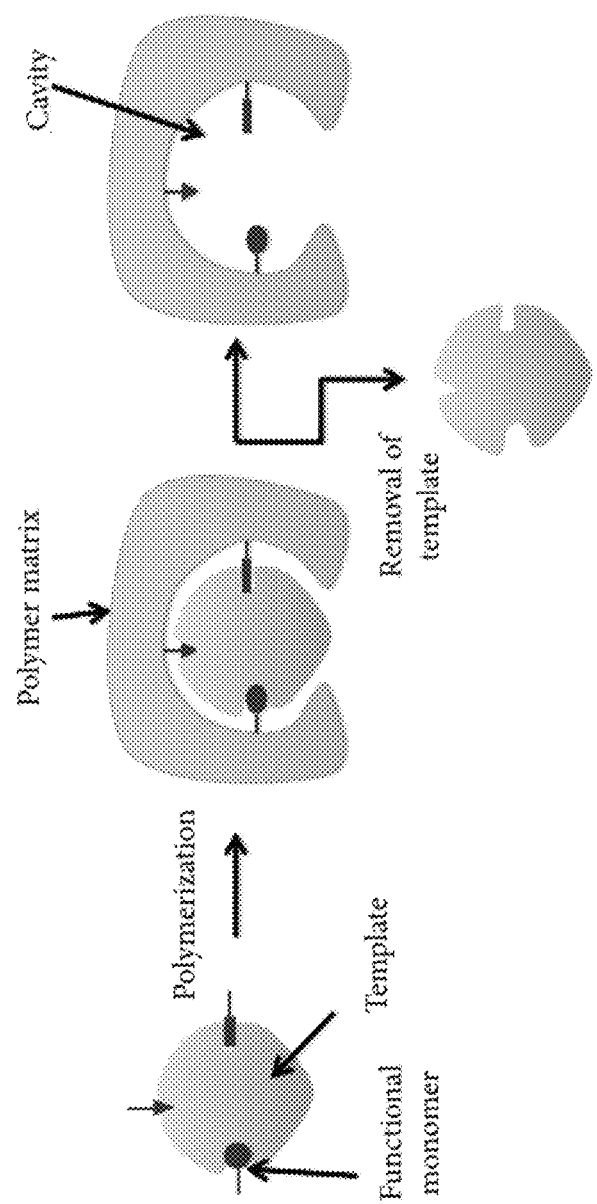
FIG. 2 is a schematic of molecular imprinting technology, and shows a process by which a molecularly imprinted polymer (MIP) can be made.

As used herein, "molecularly imprinted polymer," or "MIP," refers to a polymer created using molecular imprinting technology. The polymeric matrix of a "molecularly imprinted polymer" is characterized by molecular recognition sites specific to one or more analytes that enable the MIP to selectively bind the one or more analytes. FIG. 2 is a schematic of molecular imprinting technology, which can be used to make MIPs. Briefly, a template molecule is placed in solution with a polymerizable monomer. Polymerization is initiated upon application of voltage. After the polymerization, a washing agent can be used to remove the template molecules, and to reveal cavities that trap the same size and shape of molecule as the template molecule. Molecular imprinting technologies for creating MIPs are well-known in the art, and described in the Exemplification herein, as well as in Saylan, Y., et al., "Molecular Imprinting of Macromolecules for Sensor Applications," *Sensors*, 2017, 17, 898; Erturk, G. and Mattiasson, B., "Molecular Imprinting Techniques Used for the Preparation of Biosensors," *Sensors* 2017, 17, 288; and Chen, L., et al., "Molecular imprinting: perspectives and applications," *Chem. Soc. Rev.*, 2016, 45, 2137, the relevant teachings of which are incorporated herein by reference in their entireties.

It will be understood that, though a device may be described as being selective for an analyte, the selectivity of the device is mediated or substantially mediated by the MIP of the device. As used herein, a MIP or device described herein including a MIP "selectively binds" or "is selective for" an analyte if the MIP binds to the analyte to a greater extent than at least one other, different analyte. In some aspects, the MIP binds to its one or more cognate analytes at least two-fold, at least five-fold, at least ten-fold, or at least fifty-fold more strongly than the at least one other, different analyte. In some aspects, the MIP does not bind to the at least one other, different analyte to any measurable degree.

As described above, a MIP or device described herein including a MIP is selective for one or more analytes (e.g., 1, 2, 3, 4, 5, 6, 7, 8, 9, 10, etc.). In some aspects, the MIP or device including the MIP is selective for one analyte (e.g., butylated hydroxytoluene (BHT), nonane, pivalic acid, hexanal, heptane, benzene). In some aspects, the MIP or device including the MIP is selective for more than one analyte, as in an array. For example, the MIP or device including the MIP is selective for a set or subset of analytes associated with a particular disease or disorder.

Typically, the one or more analytes will be in fluid (i.e., liquid or gas) form. In some aspects, the one or more analytes are in gas form. In some aspects, the one or more analytes are in liquid form.

In some aspects, the one or more analytes are each a volatile organic compound. As used herein, "volatile organic compound" refers to any organic compound having a boiling point less than or equal to 250° C. measured at an atmospheric pressure of 101.3 kPa. Common examples of volatile organic compounds include, but are not limited to, acetone, acetic acid, butanal, carbon disulfide, ethanol, isopropyl alcohol, formaldehyde and methylene chloride. The United States Environmental Protection Agency also maintains a list of volatile organic compounds, which can be accessed at https://iaspub.epa.gov/sor_internet/registry/substreg/search-andretrieve/advancedsearch/search.do?details=displayDetails&selectedSubstanceId=83723.

In some aspects, the one or more analytes has a molecular weight of less than about 3,000 daltons, less than about 1,000 daltons or less than about 500 daltons. Though MIPs selective for compounds up to about 3,000 daltons are routinely prepared, MIPs selective for larger analytes, such as peptides, carbohydrates and proteins, can also be prepared. These analytes, too, are meant to be encompassed herein.

In some aspects, the one or more analytes are associated with a disease or condition. Devices comprising MIPs selective for one or more disease- or condition-associated analytes (e.g., disease- or condition-associated volatile organic compounds) can conveniently be used as diagnostic devices to detect analyte(s) associated with a particular disease or condition and thereby diagnose a subject having the disease or condition. Potential sources of analytes associated with a disease or condition include the breath (e.g., exhaled breath), sweat, blood and urine of a subject.

As used herein, "disease" refers to any condition that impairs the normal functioning of the body. Example diseases include, but are not limited to, malignant diseases (e.g., lung cancer, gastric cancer, head and neck cancer, breast cancer, colon cancer, prostate cancer, liver cancer), neurological diseases (e.g., Alzheimer's disease, Parkinson's disease, multiple sclerosis), metabolic disorders (e.g., diabetes, hyperglycemia, phenylketonuria, methionine malabsorption syndrome, hypermethioninemia, trimethylaminuria), asthma, chronic obstructive pulmonary disease, halitosis, inflammatory bowel disease, heart failure, hepatic encephalopathy, liver fetor, chronic renal failure, schizophrenia or a communicable disease (e.g., bladder infection, cholera, chronic hepatitis, intestinal problems, such as bacterial and colonic fermentation, bacterial infection, tuberculosis, urinary tract infection). In some aspects, the disease is Alzheimer's disease. In some aspects, the disease is lung cancer.

As used herein, "condition" refers to any disease, illness or injury. Example conditions include, but are not limited to, diseases described herein.

When an analyte is "associated with a disease or condition," the analyte has been linked to or otherwise implicated in a particular disease or condition, e.g., as a symptom of the disease or condition. An analyte associated with a disease or condition can be differentially present (e.g., present in larger quantities, detectable, present) in diseased subjects or differentially absent (e.g., present in lesser quantities, undetectable, completely absent) in diseased subjects compared to their healthy counterparts. For example, certain volatile organic compounds have been shown to be differentially present in the breath of Alzheimer's disease patients as compared to their healthy counterparts. See, for example, Tisch, U., et al., "Detection of Alzheimer's and Parkinson's disease from exhaled breath using nanomaterial-based sensors," *Nanomedicine* 2013, 8(1), 43-56; and Broza, Y. Y. and Haick, H., "Nanomaterial-based sensors for detection of disease by volatile organic compound," *Nanomedicine*, 2013, 8(5), 785-806, the relevant teachings of which are incorporated herein by reference in their entireties.

In some aspects, the disease is Alzheimer's disease and/or the one or more analytes are styrene; 1-methyl-2-(1-methylethyl)-benzene; 4-methyl-octane; 2,6,10-trimethyl-dodecane; 3,7-dimethyldecane; butylated hydroxytoluene; 2,4-dimethyl-1-heptene; 2,3-dimethylheptane; propyl-benzene; 2,2,4,6,6-pentamethylheptane; 2,5,6-trimethyloctane; 5-ethyl-2-methyloctane; 2,6,10,14-tetramethylhexadecane; 3,7-dimethylpropanoate (E)-2,6-octadien-1-ol; 2,3,5-trimethylhexane; (1-methylethyl)benzene; (1-methylpropyl)cyclooctane; 2,2-dimethylpropanoic acid; 2-ethylhexyl tetradecyl ester oxalic acid; 2-butyl-1-octanol; dodecane; 1-chloro-nonadecane; 3-ethyl-2,2-dimethyl-pentane; or 1,1'-oxybis-octane, or a combination of the foregoing.

In some aspects, the disease is lung cancer, and/or the one or more analytes are pentane; heptane; octane; decane; 2-methylpentane; 2,3,3-trimethylpentane; 2,3,5-trimethyl hexane; 2,4-dimethyl-1-heptane; 4-methyloctane; 2,4-dimethyl-1-heptene; isoprene; 1-propanol; 2-ethyl-1-hexanol; formaldehyde; acetaldehyde; propanal; butanal; pentanal; hexanal; heptanal; octanal; nonanal; 2-methylpropanal; methacrylaldehyde; 2-methylbutanal; 3-methylbutanal; 2-methyl-2-butenal; acetone; 2-butanone; 2-petanone; butyl acetate; acetonitrile; benzene; toluene; styrene; or 2,5-dimethyl-furan, or a combination of the foregoing.

In some aspects, the disease is gastric cancer, and/or the one or more analytes are 2-propenenitrile; 2-butoxy-ethanol; furfural; 2-pentyl acetate; 6-methyl-5-hepten-2-one; isoprene; or 4,5-dimethyl-nonane, or a combination of the foregoing.

In some aspects, the disease is head and neck cancer, and/or the one or more analytes are 4,6-dimethyl-dodecane; 2,2-dimethyl-propanoic acid; 5-methyl-3-hexanone; 2,2-dimethyl-decane; limonene; or 2,2,3-erimethyl-exobicyclo(2,2,1)heptane, or a combination of the foregoing.

In some aspects, the disease is breast cancer, and/or the one or more analytes are 3,3-dimethyl pentane; 2-amino-5-isopropyl-8-methyl-1-azulenecarbonitrile; 5-(2-methylpropyl)nonane; or 2,3,4-trimethyldecane, or a combination of the foregoing.

In some aspects, the disease is colon cancer, and/or the one or more analytes are 1,1'-(1-butenylidene)bisbenzene; 1-iodononane; ([1,1-dimethylethyl]thio)acetic acid; 4-(4-propylcyclohexyl)-4'-cyano(1,1"-biphenyl)-4-yl ester benzoic acid; or 2-amino-5-isopropyl-8-methyl-1-azulenecarbonitrile, or a combination of the foregoing.

In some aspects, the disease is prostate cancer, and/or the one or more analytes are toluene; 2-amino-5-isopropyl-8-methyl-1-azulenecarbonitrile; p-xylene; or 2,2-dimethyl decane, or a combination of the foregoing.

In some aspects, the disease is Alzheimer's disease, and/or the one or more analytes are styrene; 2,3,6,7-tetramethyl-octane; butylated hydroxytoluene; 5-ethyl-2-methyl-octane; decamethylcyclopentasiloxane; ethylbenzene; 1-methyl-3-(1-methylethyl)-benzene; 3,7-dimethyl-decane; 2,3-dimethyl-heptane; 5-ethyl-2-methyl-octane; 2,3,5-trimethyl-hexane; or hexadecane, or a combination of the foregoing.

In some aspects, the disease is multiple sclerosis, and/or the one or more analytes are hexanal or 5-methyl-undecane, or a combination of the foregoing.

In some aspects, the disease is diabetes, and/or the one or more analytes are acetone, ethanol or methyl nitrate, or a combination of the foregoing.

In some aspects, the disease is hyperglycemia, and/or the one or more analytes are methyl nitrate, xylene, or ethyl-benzene, or a combination of the foregoing.

In some aspects, the disease is hypermethioninemia, and/or the one or more analytes are dimethyl sulfide.

In some aspects, the disease is trimethylaminuria, and/or the one or more analytes are trimethylamine.

In some aspects, the disease is asthma, and/or the one or more analytes are pentane, ethane, 8-isoprostane, nitric oxide, ammonia or hydrogen peroxide, or a combination of the foregoing.

In some aspects, the disease is chronic obstructive pulmonary disease, and/or the one or more analytes are nitric oxide; ethane; isoprene; 4,7-dimethylundecane; 2,6-dimethylheptane; 4-methyloctane; or hexadecane, or a combination of the foregoing.

In some aspects, the disease is halitosis, and/or the one or more analytes are hydrogen sulfide; methyl mercaptan; dimethyl sulfide; allylmercaptan; allyl methyl sulfide; propyl mercaptan; ethyl propyl sulfide; carbon disulfide; ammonia; dimethyl amine; trimethyl amine; skatole; or N-butyric acid, or a combination of the foregoing.

In some aspects, the disease is inflammatory bowel disease, and/or the one or more analytes are pentane, ethane, or propane, or a combination of the foregoing.

In some aspects, the disease is heart failure, and/or the one or more analytes are nitric oxide.

In some aspects, the disease is liver fetor, and/or the one or more analytes are dimethyl sulfide; methylmercaptan; carbonyl sulfide; or acetaldehyde, or a combination of the foregoing.

In some aspects, the disease is chronic renal failure, and/or the one or more analytes are dimethylamine; trimethylamine; ammonia; 2-butanone; 2,4-dimethyl-heptane; or 2,2,6-trimethyloctane, or a combination of the foregoing.

In some aspects, the disease is schizophrenia, and/or the one or more analytes are carbon disulfide or pentane, or a combination of the foregoing.

In some aspects, the disease is chronic hepatitis, and/or the one or more analytes are methylmercaptan or dimethylsulfide, or a combination of the foregoing.

In some aspects, the disease is intestinal problems, such as bacteria and colonic fermentation, and/or the one or more analytes are methane or ethanol, or a combination of the foregoing.

In some aspects, the disease is tuberculosis, and/or the one or more analytes are methyl nicotinate; methyl-phenylacetate; methyl p-anisate; O-phenylanisole; 3-(1-methylethyl)-oxetane; 4-methyldodecane; hexyl-cyclohexane; bis-(3,5,5-trimethylhexyl)phthalate; 1,3,5-trimethylbenzene; 3,7-dimethyl-decane; tridecane; 4,6,8-trimethyl-1-nonene; 5-ethyl-2-methylheptane; or 4-methyl-1-hexene, or a combination of the foregoing.

Other diseases, and their associated analytes, are described in Broza, Y. Y. and Haick, H., "Nanomaterial-based sensors for detection of disease by volatile organic compound," *Nanomedicine*, 2013, 8(5), 785-806, the relevant teachings of which are incorporated herein by reference in their entireties.

In some aspects, the device has a thickness of about 5 millimeters or less, about 2.5 millimeters or less, or about 1 millimeter or less. In a particular aspect, the device has a thickness of about 1 millimeter.

In some aspects, the device has a length and a width, and is about 50 millimeters or less (e.g. about 5 millimeters or less) in length, and about 50 millimeters or less (e.g., about 5 millimeters or less) in width.

In some aspects, the device further comprises one or more electrical contacts in electrical communication with the layer of molecularly imprinted polymer. Accordingly, another embodiment is a device comprising one or more layers of metal (e.g., one layer of metal) on a layer of silicon; a layer of molecularly imprinted polymer in electrical communication with the one or more layers of metal; and one or more electrical contacts. The electrical contacts are in electrical communication with the layer of molecularly imprinted polymer. Another embodiment is a device comprising one or more layers of metal (e.g., one layer of metal) on a layer of silicon; one or more layers of graphene on the one or more layers of metal; a layer of molecularly imprinted polymer on the one or more layers of graphene; and one or more electrical contacts. The one or more layers of graphene are in electrical communication with the one or more layers of metal and the layer of molecularly imprinted polymer, and the electrical contacts are in electrical communication with the layer of molecularly imprinted polymer.

Suitable materials for the electrical contacts include, but are not limited to, gold and silver. Accordingly, in some aspects, the electrical contacts comprise gold. In some aspects, the electrical contacts comprise silver.

One embodiment is a device, comprising a layer of silicon having a thickness of from about 100 microns to about 1 millimeter; a layer of chromium on the layer of silicon, the layer of chromium and the layer of silicon having a combined resistance of about 60 ohms; from about 5 to about 15 layers of graphene on the layer of chromium and in electrical communication with the layer of chromium; a layer of molecularly imprinted polypyrrole on the layers of graphene and in electrical communication with the layers of graphene; and one or more electrical contacts in electrical communication with the layer of molecularly imprinted polypyrrole. The layers of graphene comprise potassium ferrocyanide. The device is about 5 millimeters or less in length, about 5 millimeters or less in width, and about 5 millimeters or less in height; and has a resistance of from about 10 ohms to about 100 ohms.

The devices described herein can be conveniently incorporated into systems for use by appropriate personnel (e.g., medical personnel, subjects suspecting they have a disease or condition intended to be diagnosed by the device). Accordingly, one embodiment is a system comprising a device described herein and an ohmmeter in electrical contact with the device. In some aspects, the system further comprises a microcontroller unit capable of monitoring and transmitting data obtained from the ohmmeter (e.g., via BLUETOOTH® technology to a smart phone, for example).

Also provided herein are methods involving the disclosed devices. One embodiment is a method of detecting one or more analytes in a sample (e.g., a breath, sweat, blood or urine sample, especially a breath sample, obtained from a subject). The method comprises measuring the resistance of a device described herein that has been or is in contact with a sample. The device has an inherent resistance, and is selective for one or more analytes. A difference between the inherent resistance of the device and the resistance of the device contacted with the sample indicates the presence of at least one of the one or more analytes in the sample.

Another embodiment is a method of detecting one or more analytes associated with a disease or condition in a subject suspected to have the disease or condition, or at risk for developing the disease or condition. The method comprises measuring the resistance of a device described herein that has been or is in contact with a sample (e.g., a breath, sweat, blood or urine sample, especially a breath sample) obtained from the subject. The device has an inherent resistance, and is selective for one or more analytes associated with the disease or condition. A difference between the inherent resistance of the device and the resistance of the device contacted with the sample indicates one or more analytes associated with the disease or condition have been detected.

Another embodiment is a method of diagnosing a disease or condition in a subject suspected to have the disease or condition, or at risk for developing the disease or condition. The method comprises measuring the resistance of a device described herein that has been or is in contact with a sample (e.g., a breath, sweat, blood or urine sample, especially a breath sample) obtained from the subject. The device has an inherent resistance, and is selective for one or more analytes associated with the disease or condition. A difference between the inherent resistance of the device and the resistance of the device contacted with the sample indicates the subject has the disease or condition.

As used herein, "inherent resistance" refers to the resistance of a device described herein in the absence or substantial absence of the one or more analytes for which the device is selective. A person of ordinary skill in the art will appreciate that the methods described herein can be carried out by comparing the inherent resistance of the device (e.g., as an absolute number) to the resistance of the device contacted with a sample (e.g., also as an absolute number), such that the magnitude of the difference, if calculated, is the mathematical difference between the inherent resistance and the resistance of the device contacted with the sample. Alternatively, resistance can be based on a normalized scale, for example, using the following equation: $[(R-R_0)/R_0] \times 100$, where R is the resistance of the device contacted with a sample and $R_0$ is the inherent resistance of the device. When normalized resistance is used, the device still has an inherent resistance associated with an absolute value, but the inherent resistance is assigned a value of zero. Using this method of comparing inherent resistance and resistance of a device contacted with a sample, the change in the resistance of the device (e.g., upon exposure to a sample) is the mathematical difference between the inherent resistance of the device and the resistance of the device contacted with the sample. The methods described herein contemplate and include both methods, and either understanding of "inherent resistance."

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some aspects, the subject is a mammal. In some aspects, the subject is a human.

A person of ordinary skill in the art will be able to identify those subjects suspected to have a disease or condition detectable and/or diagnosable with a device described herein, for example, based on a subject's symptoms, other tests or analyses, etc. A person of ordinary skill in the art will be able to identify those subjects at risk for developing a disease or condition detectable and/or diagnosable with a device described herein, for example, based on genetic information, family history or other factors known to a person of ordinary skill in the art.

Analytes, diseases and conditions for the methods described herein are as described throughout this application.

In some aspects, the methods further comprise contacting the device with the sample.

The devices described herein typically show linear behavior over the relevant range of analyte (e.g., the range of analyte expected to be present in a sample, such as a sample obtained from a subject). Accordingly, in many cases, the mathematical difference between the inherent resistance of a device described herein (however measured), and the resistance of a device contacted with a sample, can be translated into analyte quantity. In some aspects, the methods described herein further comprise calculating the amount of the analyte in the sample using the measured resistance.

In some aspects, the resistance of the device is measured while the device is in contact with the sample.

In some aspects, the methods described herein further comprise providing a chamber containing the device and into which the subject exhales, thereby contacting the device with the sample. In particular aspects, the chamber is sealed or substantially sealed.

The devices and methods described herein can also be used to diagnose a disease or condition in which the analyte to be detected is differentially absent in diseased subjects compared to their healthy counterparts. Thus, in one embodiment, a method of diagnosing a disease or condition in a subject suspected to have the disease or condition, or at risk for developing the disease or condition is provided. The method comprises measuring the resistance of a device described herein that has an inherent resistance, and has been or is in contact with a sample (e.g., a breath, sweat, blood or urine sample, especially a breath sample) obtained from the subject. Here, a lack of difference, or a difference of insufficient magnitude between the inherent resistance of the device and the resistance of the device contacted with the sample indicates the subject has the disease or condition. A difference of insufficient magnitude can be assessed by comparing the difference measured to the difference expected based on a healthy subject or a population of healthy subjects, optionally taking into account any error associated with the method.

In some aspects, the methods further comprise comparing the resistance of a device contacted with a sample according to the methods described herein, or an amount of analyte calculated from the resistance of a device contacted with a sample according to the methods described herein to the resistance of a device contacted with a sample from a healthy subject or a population of healthy subjects or the amount of analyte in a comparable sample from a healthy subject or population of healthy subjects, respectively, or a relevant standard (e.g., a standard range) based on a healthy subject or population of healthy subjects. A difference (e.g., a clinically significant difference, a statistically significant difference, a difference taking into account any error associated with the method) between the sample and the relevant comparator indicates the subject has the disease or condition.

In some aspects, the methods further comprise comparing the resistance of a device contacted with a sample according to the methods described herein, or an amount of analyte calculated from the resistance of a device contacted with a sample according to the methods described herein to the resistance of a device contacted with a sample from a subject or a population of subjects having the disease or condition or the amount of analyte in a comparable sample from a subject or population of subjects having the disease or condition, respectively, or a relevant standard (e.g., a standard range) based on a subject or population of subjects having the disease or condition. A lack of difference (e.g., a difference of insufficient magnitude, optionally taking into account any error associated with the method; a clinically insignificant difference, a statistically insignificant difference) between the sample and the relevant comparator indicates the subject has the disease or condition.

Methods of making the devices disclosed herein are also provided. One embodiment is a method of making a device, comprising applying one or more layers of metal to a layer of silicon; and applying a layer of molecularly imprinted polymer to the device such that the layer of molecularly imprinted polymer is in electrical communication with the one or more layers of metal. The one or more layers of metal are each independently selected from a layer of chromium, platinum, gold, nickel, cobalt, tungsten, rhodium, iridium, silver, tin, titanium or tantalum, or an alloy thereof. Molecularly imprinted polymers, alternative metals and other variations on the device are as described herein.

In some aspects, the one or more layers of metal are sputtered onto the layer of silicon.

In some aspects, the method of making further comprises applying one or more layers of graphene to the one or more layers of metal. Thus, one embodiment is a method of making a device, comprising applying one or more layers of metal to a layer of silicon; applying one or more layers of graphene to the one or more layers of metal; and applying a layer of molecularly imprinted polymer to the device such that the layer of molecularly imprinted polymer is in electrical communication with the one or more layers of metal. The one or more layers of metal are each independently selected from a layer of chromium, platinum, gold, nickel, cobalt, tungsten, rhodium, iridium, silver, tin, titanium or tantalum, or an alloy thereof. In some aspects, the one or more layers of graphene comprise potassium ferrocyanide. Molecularly imprinted polymers, alternative metals and other variations on the device are as described herein.

In some aspects, the layer of molecularly imprinted polymer is applied to the one or more layers of graphene. Thus, one embodiment is a method of making a device, comprising applying one or more layers of metal to a layer of silicon; applying one or more layers of graphene to the one or more layers of metal; and applying a layer of molecularly imprinted polymer to the one or more layers of graphene such that the layer of molecularly imprinted polymer is in electrical communication with the one or more layers of metal. The one or more layers of metal are each independently selected from a layer of chromium, platinum, gold, nickel, cobalt, tungsten, rhodium, iridium, silver, tin, titanium or tantalum, or an alloy thereof. In some aspects, the one or more layers of graphene comprise potassium ferrocyanide. In some aspects, the layer of molecularly imprinted polymer is applied to the device using electrochemical polymerization. Molecularly imprinted polymers, alternative metals and other variations on the device are as described herein.

In some aspects, the method of making further comprises applying electrical contacts to the device such that the electrical contacts are in electrical communication with the layer of molecularly imprinted polymer. In some aspects, the electrical contacts are applied to the layer of molecularly imprinted polymer. Electrical contacts are as described herein.

EXEMPLIFICATION

Example 1. A Molecularly-Imprinted Electrochemical Gas Sensor to Sense Butylated Hydroxytoluene in Air Abstract. Alzheimer's disease (AD) is a neurodegenerative disease that affects millions of people worldwide. Curing this disease has not gained much success so far. Exhaled breath gas analysis offers an inexpensive, non-invasive and immediate method for detecting a large number of diseases, including AD. A new method is proposed to detect butylated hydroxytoluene (BHT) in the air, which is one of the chemicals found in the breath print of AD patients. A three-layer sensor was formed through deposition of a thin layer of graphene onto a glassy carbon substrate. Selective binding of the analyte was facilitated by electrochemically-initiated polymerization of a solution containing the desired target molecule. Subsequent polymerization and removal of the analyte yielded a layer of polypyrrole, a conductive polymer, on top of the sensor containing molecularly imprinted cavities selective for the target molecule. Two sets of sensors have been developed. First, a graphene sensor was fabricated with a layer of reduced graphene oxide (RGO) and tested over a BHT concentration range of 5-100 parts per million (ppm). For the second sensor, Prussian blue was added to graphene before polymerization to enhance its electrochemical properties. The second sensor was tested over a BHT concentration range of 0.02-1 parts per billion (ppb) while the sensor resistance was monitored.

Introduction. Alzheimer's disease (AD) is the sixth cause of death in the USA. In 2016, the cost of AD was evaluated as $236 billion dollars. It is known by a decline in memory, language, problem-solving, reasoning, planning and other thinking and cognitive skills. It happens when the neurons in the brain are damaged or destroyed, so data process and transmission in the brain will be spoiled. Later by spreading the disease in the brain, the patient will not be able to perform daily activities such as walking or eating. The diagnosis procedures usually take so long. It starts with the evaluation of patient's cognitive ability and reviewing medical history. It continues with lab tests and imaging techniques to visualize the damaged brain tissue. When the damaged tissue is clearly observed by MRI and CT, it is too late to cure the disease since the patient has already lost part of the brain tissues. Researchers have shown that AD starts years, if not decades, before it is diagnosed. The sooner the disease can be diagnosed, the better treatment options can be provided.

Amyloid beta (Aβ) is a peptide known as the biomarker of AD. Aggregation of Aβ in the brain is thought to initiate neurotoxic phenomena, including neuron-inflammation, synaptic and neuronal loss. Destroying the already developed and/or stopping the development of Aβ in the brain is the best option, but it has not gained much success. Some researchers tried to detect Aβ in cerebrospinal fluid (CSF), blood and exhaled breath and correlate it with AD. It has been shown that Aβ is existed in CSF and in less concentration in blood of AD patients. Detection of Aβ in the exhaled breath with enzyme-linked immunosorbent assay (ELISA) has also been tried. However, a higher level of Aβ in the healthy control's breath was found. Besides, researchers found a relationship between Aβ with narcolepsy, a sleep disorder. They detected lower CSF $A\beta_{42}$ levels in the whole narcolepsy group with respect to controls.

It was first found by Greek scientists that human breath provides clues into the physiological status of the body. Human breath is mainly composed of nitrogen, oxygen, carbon dioxide and hydrogen. VOCs are organic chemicals with high vapor pressure (at room temperature), that, along with inert gases, form less than 1% of the exhaled breath. From the physiological point of view, the exchange of blood and the air in the alveolar leads to transferring chemicals in the blood, which was formed during metabolism inside the body, to find a way to the exhaled breath. Thus, measurement of VOCs in the breath can provide a window into the biochemical processes of the body. A growing number of studies tried to demonstrate the correlation of VOCs and neurodegenerative diseases, including AD and PD. Using gas chromatography and mass spectroscopy, and comparing the breath print of the healthy people to AD patients, a list of additional chemicals was found. Butylated hydroxytoluene (BHT) was listed as a chemical found in the breath print of AD and PD patients. BHT is an aromatic benzene ring derivation that is known for its antioxidant properties. Disclosed herein is the fabrication and testing of two sets of the electrochemical gas sensor, which can sense butylated hydroxytoluene in the air. The sensors are composed of three layers: glassy carbon electrode (GCE); graphene (GR)-graphene or graphene-Prussia blue (GR-PB) and molecular imprinting polymer (MIP). FIG. 1 is a schematic of the two sensors, and shows a layer of molecularly imprinted polymer deposited on a graphene—(left sensor) or graphene-Prussian blue—(right sensor) modified surface of a glassy carbon electrode.

Glassy carbon is an advanced material of pure carbon combining glassy and ceramic properties. Its high purity, extreme corrosion resistance, impermeability to gas and liquid, high strength, high-temperature resistance, low oxidation rate and high chemical inertness make it suitable to be used frequently as electrode. Graphene is a 2D material known for its unique electrochemical and structural properties. One atom thick graphene has high thermal and electrical conductivity, chemical stability, high specific surface area, and excellent room temperature carrier mobility. These peculiar properties have highlighted the potential of applying this material in a variety of applications, such as electronics, sensors, catalysis, energy-storage devices, and drug delivery. Its two-dimensional nature leads to a high affinity between graphene and the MIP components, and makes it suitable for electron transfer between the two layers. The gas-sensing mechanism of graphene is generally described as electron donors or acceptors. This causes a change in the conductance of graphene. So layers of GR have been used to modify the surface of the electrode to improve the electron transfer. Prussian blue (PB, ferric ferrocyanide), formula $Fe_4[Fe(CN)_6]_3$, is a microcrystalline blue powder. It is an inorganic conductive material that exhibits high electrocatalytic activity and improves the electrochemical sensitivity. It has been extensively studied for its attractive electrochemical properties and wide applications in the field of sensors. In many cases, PB has been used as a mediator with graphene. Combination of GR and PB lead to a synergistic effect that can help the electron transfer.

Cyanide ion is very stable at room temperature, and the concentration of free $Fe^{+2}$ ions is negligible. However, in acidic media (pH=1.7), $Fe^{+2}$ will release from cyanide and it is then oxidized to $Fe^{+3}$. The released electrons together with H+ would react with oxygen-containing groups on GO, leading to the partial reduction of GO to rGO at room temperature. In the meantime, $Fe^{+3}$ ions interacted with carboxyl groups of GO and confined on the surface of GO. With the existence of cyanide, they form PB cubes. At the pH 1.7, the acid is not strong enough to form cyanide acid, but for precautions, it is recommended to do the procedures under the hood, respirator etc.

Table 1 summarizes the PB-GR sensors, which have been used for sensing purposes, and includes the range and limit of detection.

TABLE 1

| Modified electrode | Range of detection | Limit of detection |
| --- | --- | --- |
| Prussian blue | 0.32-5.3 µM | 0.018 µM |
| Copper-iron hexacyanoferrates | 0.3-300 µM | 0.05 µM |
| Graphene oxide/Prussian blue | 0.02-0.2 mM | 1.9 µM |
| Graphene oxide/Prussian blue | 10-1440 µM | 3 µM |
| Polyelectrolyte-functionalized ionic liquid decorated graphene sheets | 5-60 µM | 1 µM |
| Gold-Prussian blue-graphene | 0.01-3.0 mM | 1.5 µM |
| Prussian blue/reduced graphene oxide | 0.5-400 µM | 0.44 µM |
| Reduced graphene oxide/Prussian blue | 0.8-500 µM | 0.25 µM |

Molecular imprinting is a technique to polymerize around a template molecule and remove the template after polymerization. It leaves cavities with the exact size and shape of the template in the polymer matrix. Three elements in molecular imprinting technique are: the target molecule (or template) which typically corresponds to the analyte to be sensed; the functional monomer which is a compound having chemical and shape complementarity to the template and will help the polymerization to form the polymer matrix; and the cross-linking agent (or cross-linker) that is a multifunctional molecule containing two or more reactive split ends able to interact via chemical bond. The size and shape of the cavity allow the target molecule or similar molecules to occupy the cavity, but the functional monomers orientation just allows binding with the template molecule. FIG. 2 represents the MIP process.

Besides the size, shape, and orientation of functional monomers, the selectivity of MIP to the target molecule is performed by the covalent or non-covalent bonding that happens between the template molecule and the polymer matrix. In this case, hydrogen bonding between the BHT molecules and the polymer enables the creation of stable and selective "artificial receptors." It utilizes associative self-assembly between target analytes and material precursors to create a molecular "lock and key" architecture within an electrochemical sensor for ultrasensitive and selective detection. MIPs are also cost-effective, robust, long-term stable and are able to self-recover. Selectivity of MIP has been reported frequently. For example, toluene is favored by factor of six to the more bulky o-xylene; even the three xylenes can be distinguished from each other.

Figure 3:
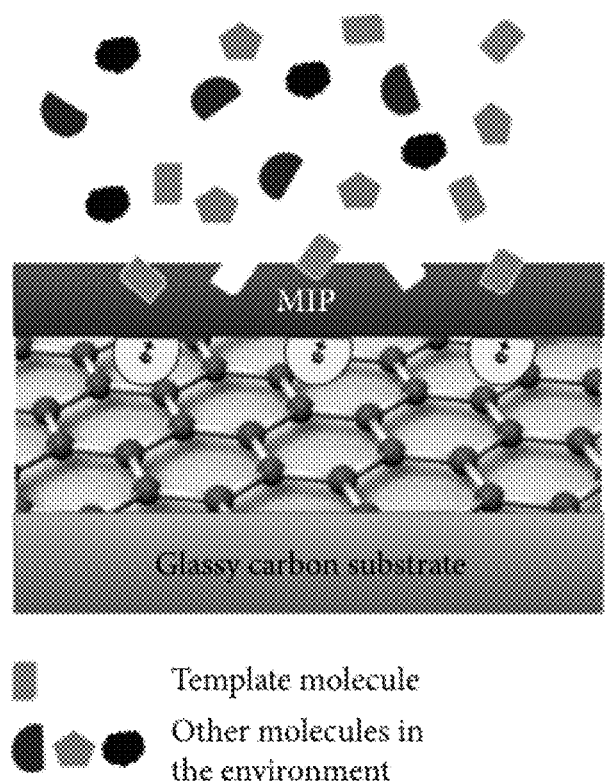
FIG. 3 is a depiction of a sensor, and shows the mechanism of the sensor. Among different molecules in the environment, only the template molecule can be absorbed in the MIP layer. When the template molecule is trapped in the MIP layer, an extra electron is transferred to the graphene layer, which causes a change in the resistance of the sensor.

Examples of common sensors for chemical sensing include surface acoustic waves (SAWs), quartz microbalance (QMB) and gold nanoparticles. SAW is elastic waves propagating along the surface of an elastic substrate, whose amplitudes decay exponentially with the substrate depth. The change in gas concentration results in a change in the mass and leads to an electrical conductivity shift of the chemical interface. These changes influence the SAW amplitude and the phase velocity. These sensors need a concentration calibration. Besides, the sensor response is not instant. In QMB sensors, a slight mass change on the quartz surface results in a frequency change of the electrical output signal of the oscillator circuit, at which each sensor is connected. The problem with QMB sensors is that the molecules with the same mass can confuse the sensor and make the same resonance frequency. Besides, the retention time can take up to several minutes and the sensitivity of the sensor is poor. Functionalized gold nanoparticles (GNPs) on field effective transistor is an electrical device that can act as a switch or can sense the gate resistance by applying an electric field to the source and the drain. It has been used to detect chemicals by adding reactant elements on the gate that can absorb the desired chemical. However, the problem with FET sensors is that it cannot absorb large chemicals. Besides, different molecules with the same reactant can mislead the sensor. MIP sensors compared to the similar ones, have huge advantages, as the molecules with the same mass or chemical properties cannot mislead the sensors, they sense instantly and, they can sense a variety of molecules from small to very large. This type of sensor includes a sensing circuit configured to detect and report resistance change in the layer of MIP. The binding of the target molecules causes the resistance change to the MIP. The sensing mechanism of this sensor is depicted in FIG. 3. Among different molecules in the environment, only the template molecule can be absorbed in the molecular imprinting polymer layer. When the template molecule is trapped in the MIP layer, an extra electron is transferred to the graphene layer, which causes a resistance change.

Materials and Methods. Two sets of electrochemical sensors were fabricated. The fabrication steps are the same, except that for the GR-PB sensor, additional steps for preparation of PB are needed. The materials and equipment are listed below.

Chemicals and Equipment. Glassy carbon plate was purchased from Alfa Aesar (MA, USA). Hydrazine hydrate, phosphate buffer solution, pyrrole, graphene oxide, and butylated hydroxytoluene were obtained from Sigma Aldrich (MO, USA). All the solutions were prepared with deionized (DI) water.

Potentiostat model Solartron SI 1287 was used to conduct the cyclic voltammetry. The potentiostat potential range was from −14.5 V to 14.5 V and the sweep rate was from 6 mV/min to 6000 V/min. Electrochemical measurements were carried out with a three-electrode system consisting of a platinum wire as the auxiliary electrode, a KCl saturated Ag/AgCl reference electrode and modified glassy carbon as the working electrode. Ultrasonicator XL 2120 and centrifuge Legend X1R were used for homogenizing and distillation of the graphene solution. The spectroscopy was done with Raman Horina HR800.

Figure 4:
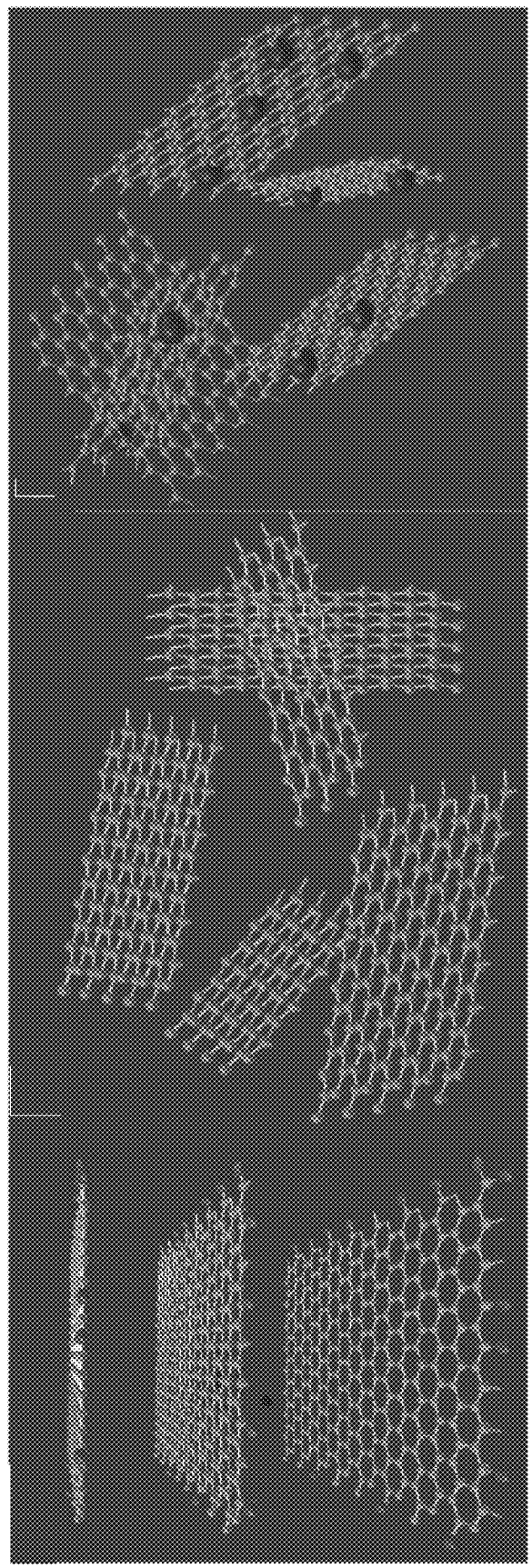
FIG. 4A depicts a stack of graphene oxide.
FIG. 4B depicts randomly oriented layers of reduced graphene oxide.
FIG. 4C depicts Prussian blue on reduced graphene oxide layers.

Graphene Synthesis. Reduced graphene oxide (RGO) was synthesized from graphene oxide (GO) based on Hummer method. In brief, the GO (500 mg) was dispersed in deionized water (500 mL) followed by ultrasonication. After that, 2 mL of hydrazine hydrate was added to the above dispersion. The obtained solution was stirred at 100° C. for 24 hours, the resulting mirror like graphene dispersion was filtered with 0.22 µm pore size filter and washed with deionized water several times. Finally, a gray layer was obtained. FIG. 4A and FIG. 4B show the procedure of obtaining reduced graphene oxide from graphene oxide.

GR-PB Preparation. Preparation of PB was according to the literature. First, 2 mg of the produced GR was added to 2 mL of deionized water and ultrasonicated to obtain a homogenous black solution. The solution was then added into 5 mL of an aqueous solution containing 0.006 g $FeCl_3 \cdot 6H_2O$, 0.008 g $K_3Fe(CN)_6$ and 0.037 g KCl (pH adjusted to 1.5 with HCl) by stirring at room temperature for 12 hours. The product was then centrifuged (2000 rpm for 20 min) and washed with the DI water several times, and dried overnight under a vacuum condition at 40° C. FIG. 4C depicts the procedures for obtaining GR-PB from GO.

Figure 5:
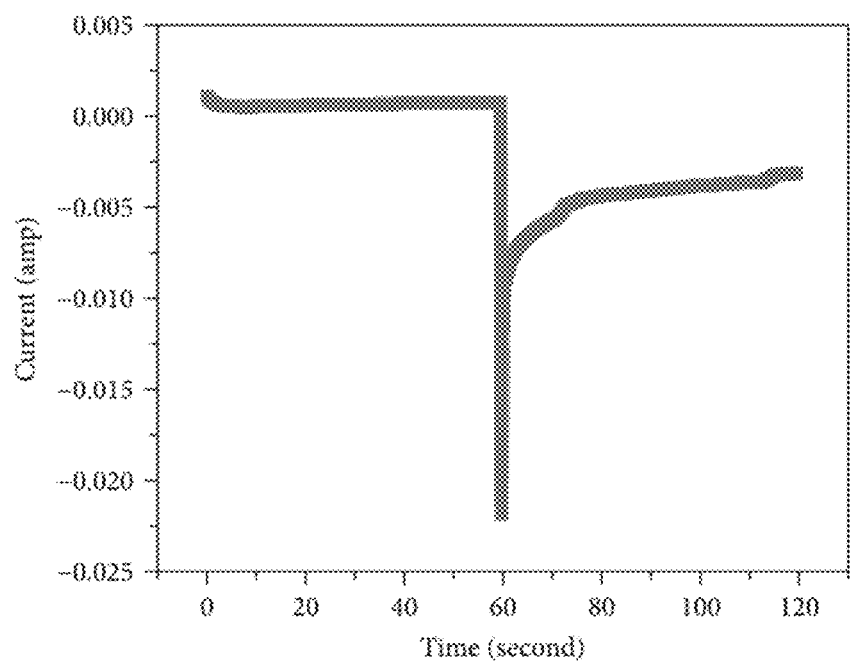
FIG. 5 is a graph of current versus time, and shows the activation process of the glassy carbon electrode (GCE) of Example 1.

Fabrication of MIP. The glassy carbon electrode (GCE) was washed and then activated by applying a pulse voltage +1.6 and −1.6 V vs Ag/AgCl for 60 seconds each. The response in current is shown in FIG. 5. The activation process was done in phosphate buffer solution (pH 6.8) using a three-electrode system, with the glassy carbon electrode as the working, Ag/AgCl as the reference and platinum as the auxiliary electrode. A large current response occurs when the potential changes to −1.6 V indicative of a reductive process of the GCE. Then, it was left to dry overnight.

Figure 6A:
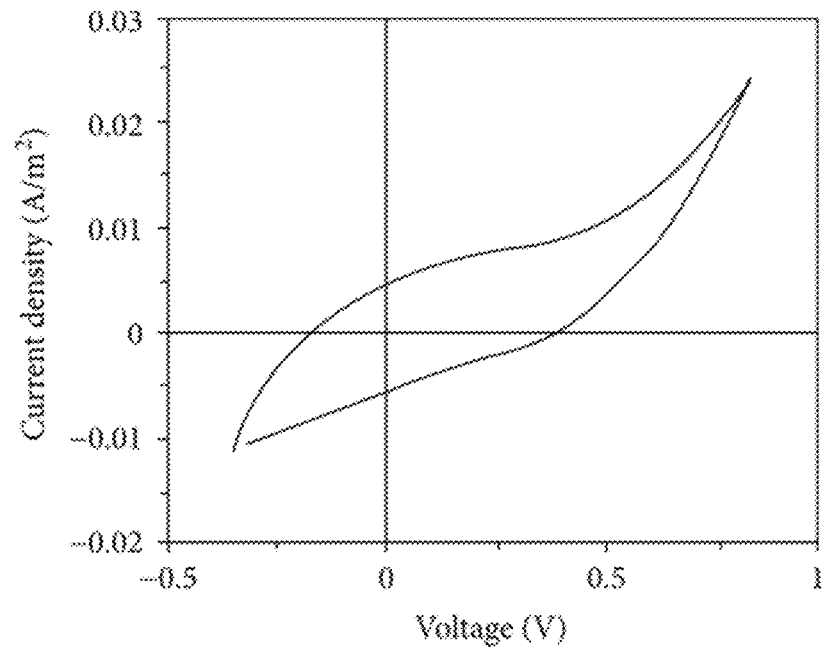
FIG. 6A is a cyclic voltammogram, and shows the last cycle of cyclic voltammetry of the polymerization process of the graphene sensor of Example 1.
Figure 6B:
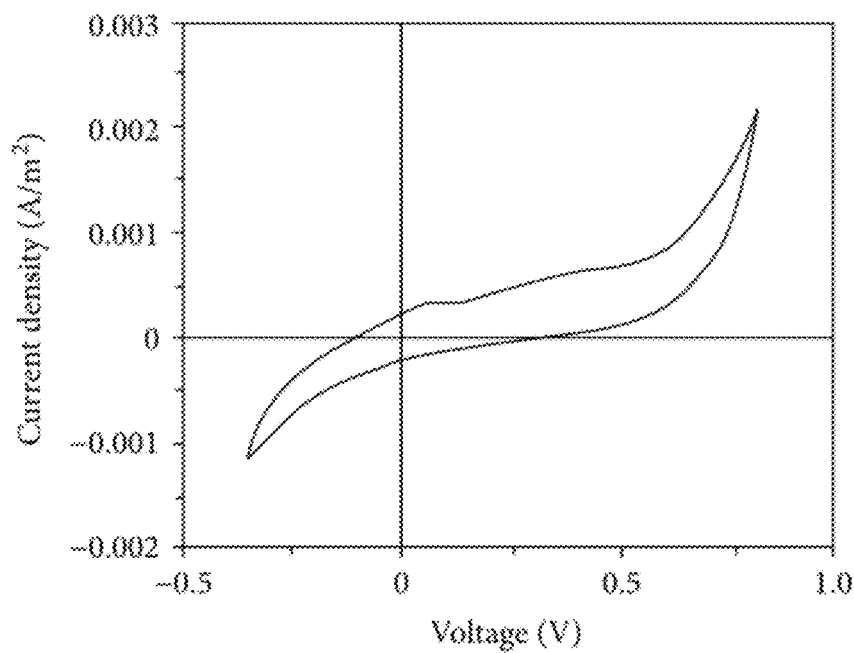
FIG. 6B is a cyclic voltammogram, and shows the last cycle of cyclic voltammetry of the polymerization process of the graphene-Prussian blue sensor of Example 1.

The GCE surface was modified by adding 2 mg of the GR-PB powder dissolved in 2 mL of DI water. It was stored overnight. A solution of 1 L phosphate buffer solution containing 0.09 BHT and 6.937 mL of pyrrole was stirred for 2 hours (pH 6.8, adjusted with HCl) to be used for cyclic voltammetry (CV). The cyclic voltammetry to deposit the polymer was carried out for 20 cycles with a scan rate of 50 mV/s, from −0.35 to +0.85 V vs. Ag/AgCl. The resulting cyclic voltammograms are shown in FIGS. 6A and 6B.

The cyclic voltammogram without PB is highly capacitive. After the polymerization process, then the sensor was washed with ethanol and left to dry overnight.

Figure 7:
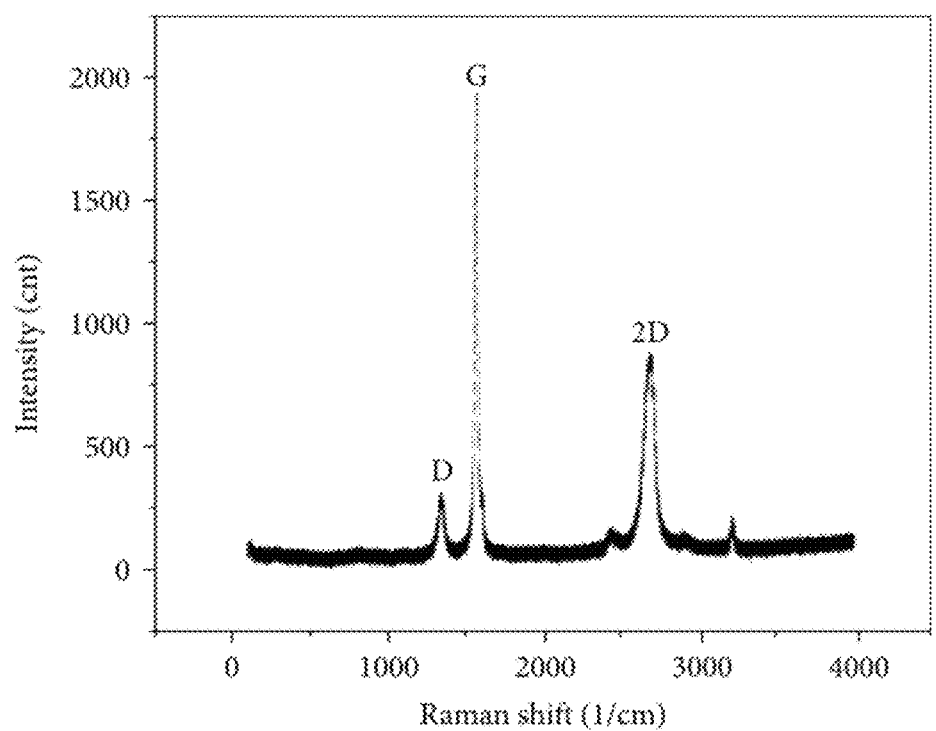
FIG. 7 is a graph, and shows the results of Raman spectroscopy analysis of the structure of reduced graphene oxide made in Example 1.

Results. Graphene Characteristic. Raman Spectroscopy is often used in chemistry to provide a structural fingerprint by which molecules can be identified. It has been applied to identify the produced RGO structure. FIG. 7 shows the results.

From Raman analysis, the D band is strong, which indicates the graphene has some defect. The full width at half maximum of the 2D band is about 80, and the intensity ratio of G/2D is more than 1, which shows that the graphene should be multilayer graphene, between 6 to 10 layers.

Testing Chamber. A sealed chamber was fabricated for the gas testing. It was made of polycarbonate 0.5-inch thick and the volume of the chamber was almost 0.5 $m^3$. The solid vapor pressure of BHT was simulated with ASPEN software. Based on the software results, a specific amount of solid BHT was left inside a syringe to evaporate. The vapor was then injected into the chamber and the sensor was given time to reach steady state before reading the resistance.

SEM Images. SEM images have been taken after removal of the templates from both sensors. The lighter color molecules on the top represent the MIP molecules. These images clearly show that GR-PB sensor has a more porous surface on top compared to GR sensor, which can lead to absorbing more template molecules. FIG. 8A and FIG. 8B show the SEM images of GR and GR-PB sensors, respectively. The GR-PB sensor has a surface more uniform, and that is because of the presence of PB.

Figure 9A:
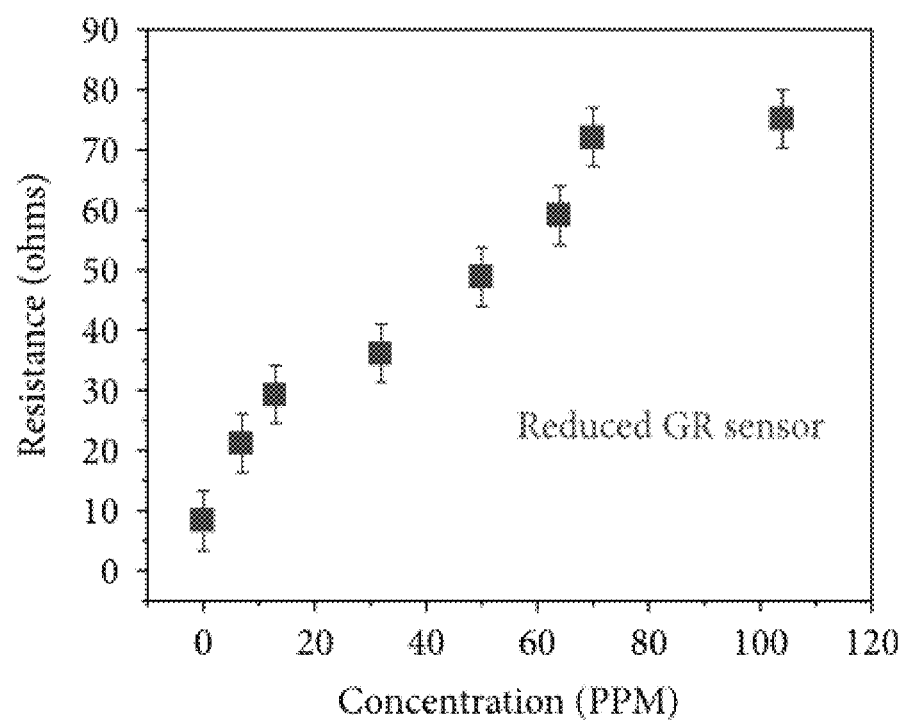
FIG. 9A is a graph of resistance versus concentration of butylated hydroxytoluene (BHT), and shows the response of the graphene sensor of Example 1 to varying concentrations of BHT.
Figure 9B:
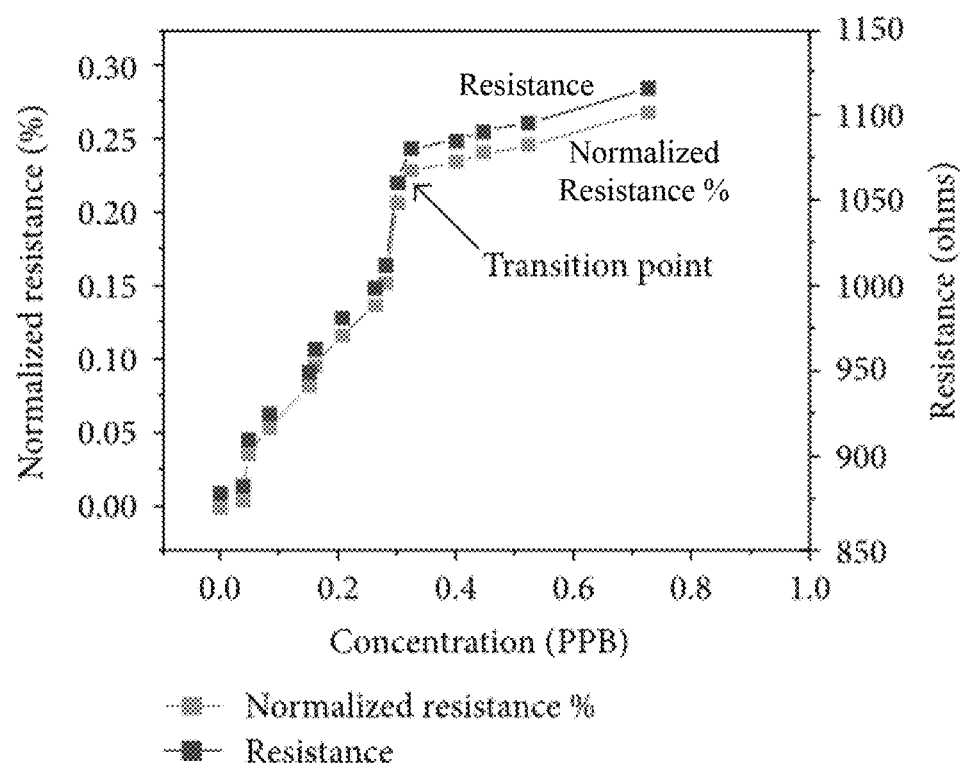
FIG. 9B is a graph of normalized resistance and resistance versus concentration of BHT, and shows the response of the graphene-Prussian blue sensor of Example 1 to varying concentrations of BHT.

Testing Results. The GR sensor was tested in the range of 5 to 100 ppm and the GR-PB sensor was tested over the range of 0.02 to 1 ppb BHT. For each measurement, a syringe of a specific vapor of BHT was injected into the chamber and it was left to reach equilibrium, while the resistance was monitored. Both sensors have almost linear behavior. The results show that Prussian blue has a huge impact on the limit of detection of the sensor. Furthermore, PB increased the sensor resistance (in the absence of any chemical), which made it easier to monitor in case of a small resistance change. The results are shown in FIGS. 9A and 9B. In the middle of the GR-PB sensor testing, the vacuum was purged into the chamber and it slowed down the resistance change. Normalized resistance was calculated based on $[(R-R_0)/R_0] \times 100$.

Figure 10:
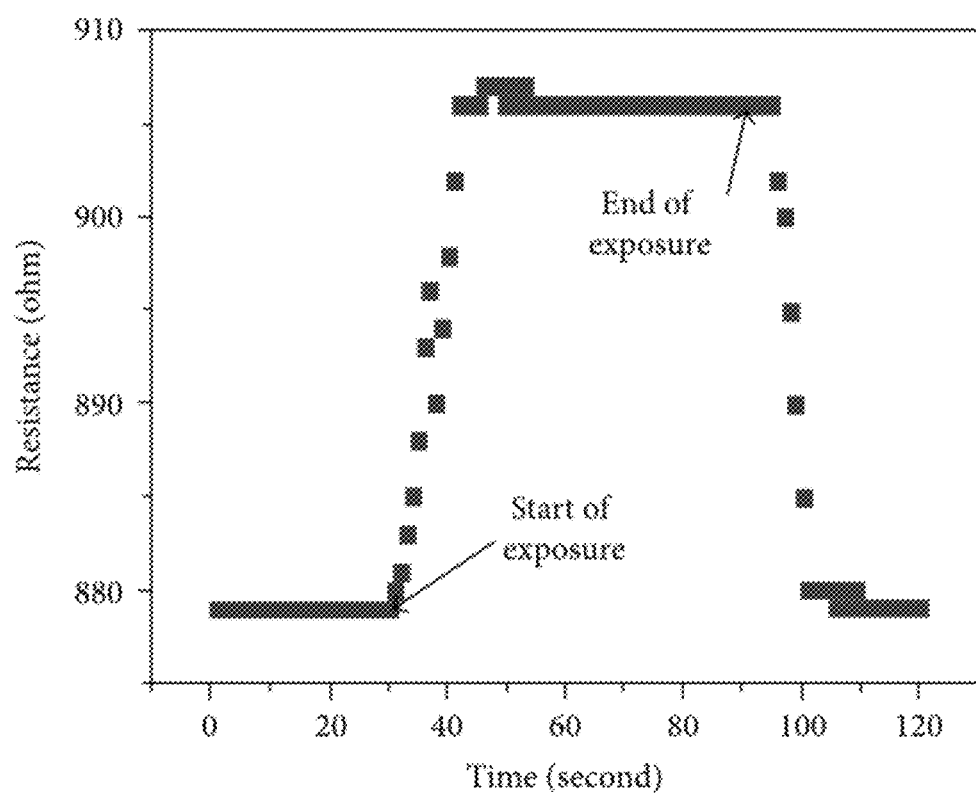
FIG. 10 is a graph of resistance versus time, and shows the behavior of the sensor of Example 1 upon exposure to BHT.

FIG. 10 shows the behavior of the sensor at the time of exposure. One-tenth mole of solid BHT was placed inside the sealed chamber at t=30 seconds, while the resistance was monitored. After one minute (at t=90 s), the solid BHT was removed from the chamber and, as shown, it took a few seconds for the sensor to return to its resting resistance. The vapor pressure of 0.1 mole BHT inside the chamber was 500 ppb, however, the time is so limited so it could not reach equilibrium.

Figure 11A:
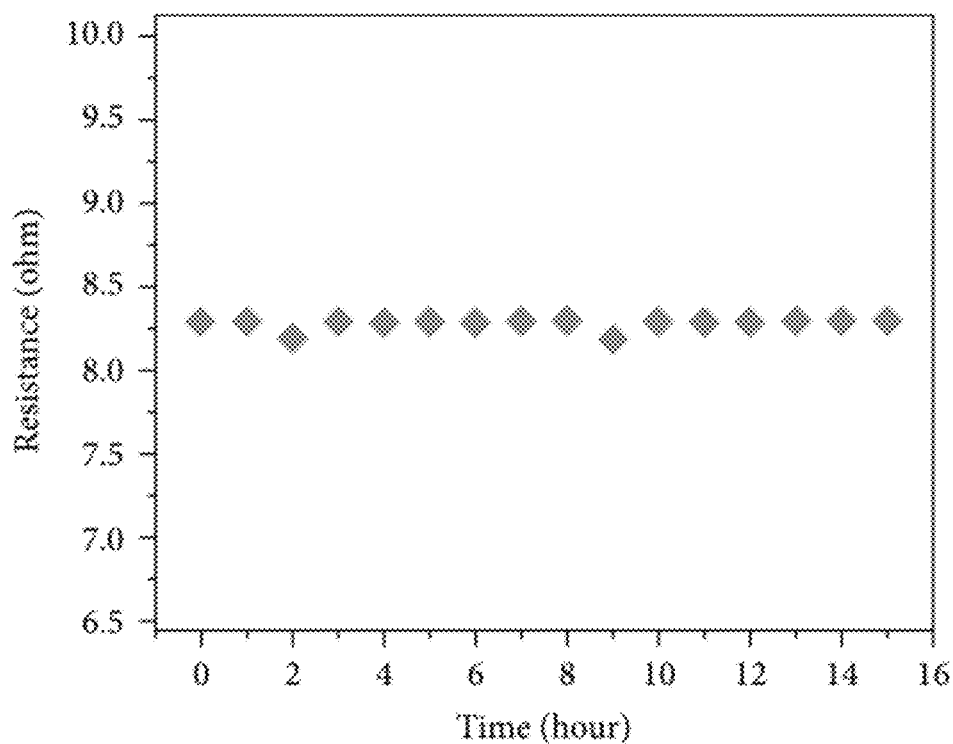
FIG. 11A is a graph of resistance versus time, and shows the stability of the graphene sensor of Example 1 over time.
Figure 11B:
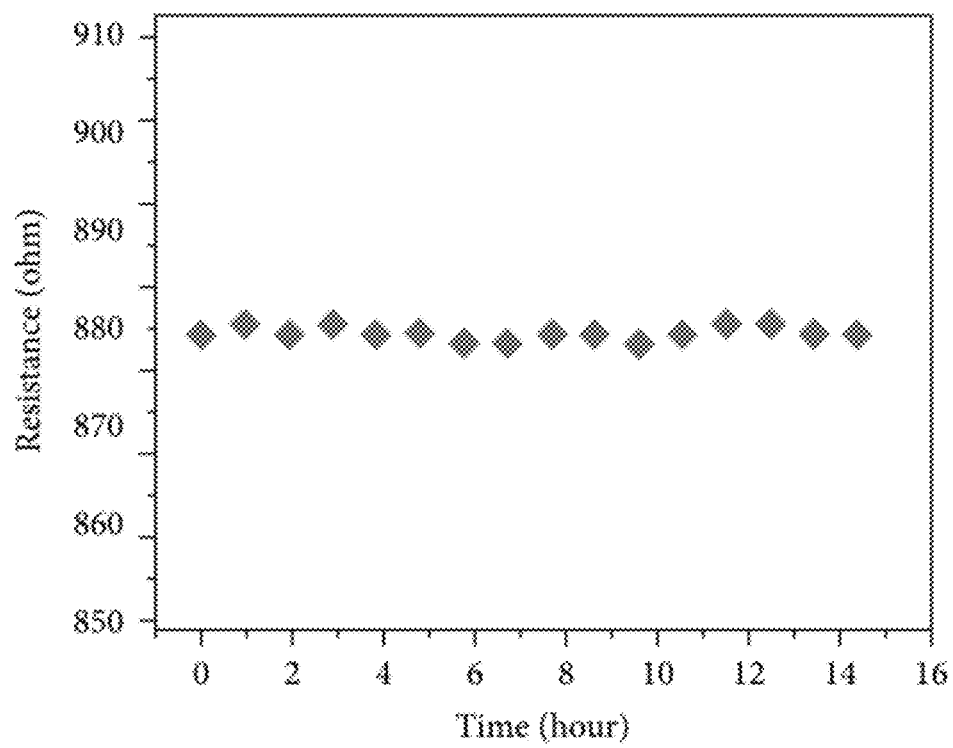
FIG. 11B is a graph of resistance versus time, and shows the stability of the graphene-Prussian blue sensor of Example 1 over time.

Before starting the test, the stability of both sensors was evaluated. The resistance of the sensors was monitored for 15 hours inside the sealed chamber in the absence of the BHT. A negligible change was observed for both sensors during the monitoring time, suggesting that both sensors are stable. FIGS. 11A and 11B show the results of the stability test.

Discussion Both sensors have been tested for sensitivity toward water vapor and nitrogen since these are the two main components of the exhaled breath. Pure nitrogen has been pumped to the sealed chamber and the sensors' responses were monitored for 10 minutes. The same experiment was done for water vapor. A beaker of 300 ml boiling water with a heater was placed inside the chamber, while the resistance was monitored for 10 minutes. Since no changes in the resistance were observed, it can be suggested that the sensors were not sensitive to nitrogen or water vapor.

The proposed PB-GR sensor is super sensitive as its limit of detection is 0.02 ppb. It is the most sensitive sensor reported so far. The concentrations of VOCs reported in the AD patients print are in the range of 1-20 ppb, so the disclosed GR-PB sensor is capable of sensing the BHT in the exhaled breath of AD patients. These gas sensors are very selective and similar molecules cannot mislead them. The fabrication steps are straightforward and can be done in a week. These low-cost sensors can be used repeatedly after being washed with ethanol.

Conclusions. Two electrochemical sensors have been fabricated to sense BHT in the air at ppm and ppb level. The graphene sensor was tested at ppm level and the graphene-Prussian blue sensor was tested at ppb level. BHT was detected at a very low concentration, less than 20 ppb, the target range for sensing it in the exhaled breath of Alzheimer's patients. The developed electrochemical sensors exhibited excellent performance such as a low limit of detection (e.g., 20 ppt), wide range of detection, high selectivity, good stability and good reproducibility toward sensing BHT. The SEM imaging showed that the GR-PB modified sensor had more porous structure than the GR-modified sensor. Besides, the testing results proved that adding PB to graphene would increase the limit of detection. It is actually because the PB exhibit high electrocatalytic activity and thus improve the electrochemical sensitivity of the sensor. The high affinity between GR and PB will increase the electron transfer between the layers. In the future, this sensor can be used as an array to detect all the chemicals found in the exhaled breath of AD patients.

Example 2. A Molecularly-Imprinted Electrochemical Gas Sensor to Detect Pivalic Acid in the Air A three-layer sensor was formed in accordance with GR-PB sensor described in Example 1, except that the MIP layer was designed to be selective for pivalic acid. Briefly, a thin layer of reduced graphene oxide-Prussian blue was deposited onto a glassy carbon substrate. Selective binding of the analyte, pivalic acid, was facilitated by electrochemically-initiated polymerization of a solution containing the desired target molecule. Subsequent polymerization and removal of the analyte yielded a layer of polypyrrole, a conductive polymer, on top of the sensor containing molecularly imprinted cavities selective for the target molecule. When the template molecule is trapped in the MIP layer, an extra electron is transferred to the graphene layer, which will cause resistance change.

Figure 12:
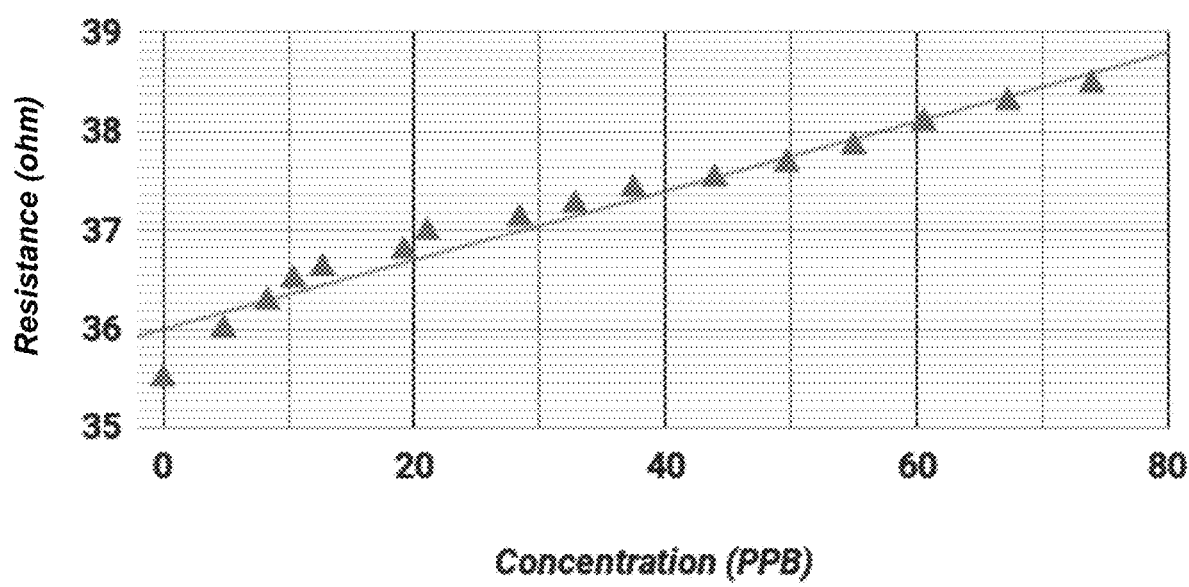
FIG. 12 is a graph of resistance versus concentration, and shows the response of the sensor of Example 2 to varying concentrations of pivalic acid.
Figure 14A:
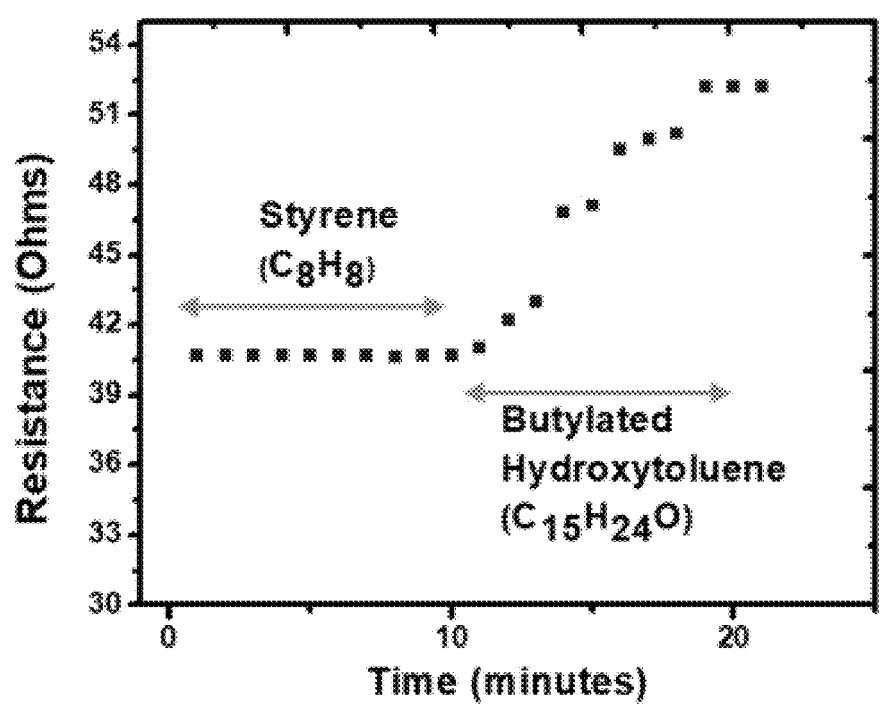
FIG. 14A is a graph of resistance versus time, and shows the results of selectivity testing of the BHT sensor of Example 3.
Figure 14C:
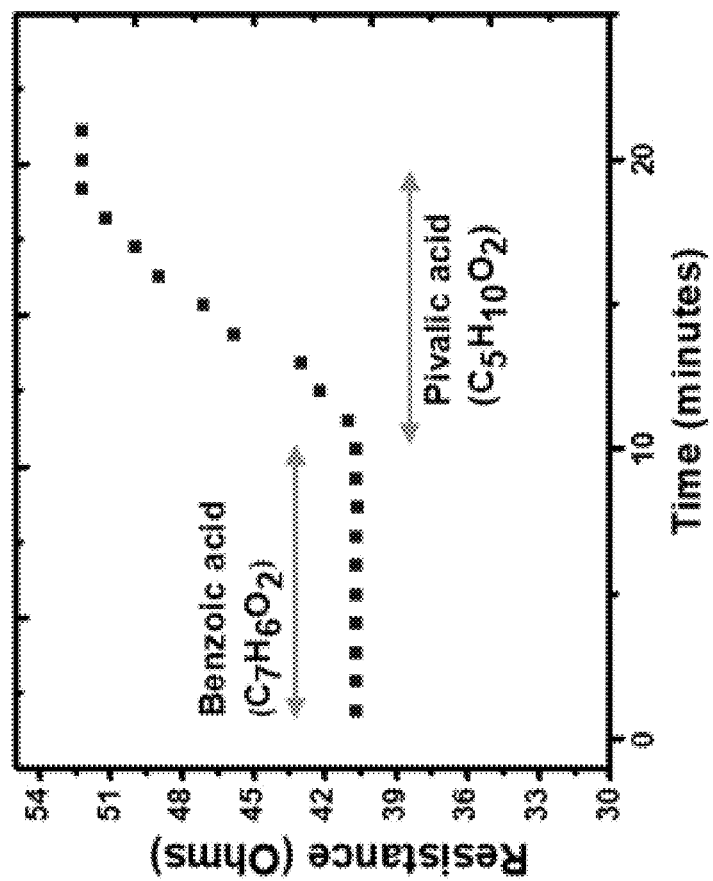
FIG. 14C is a graph of resistance versus time, and shows the results of selectivity testing of the pivalic acid sensor of Example 3.
Figure 14B:
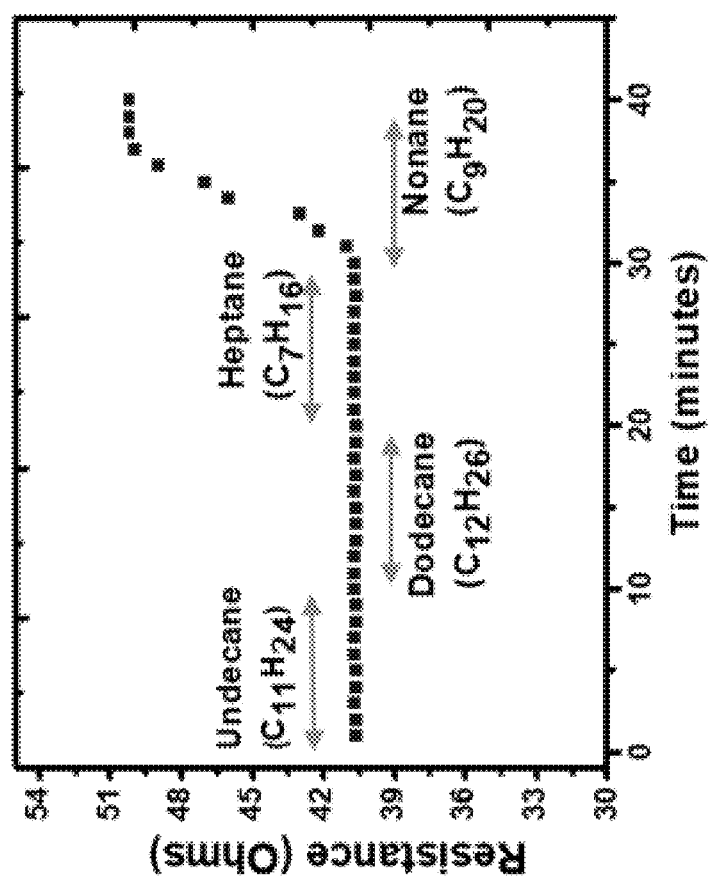
FIG. 14B is a graph of resistance versus time, and shows the results of selectivity testing of the nonane sensor of Example 3.
Figure 15A:
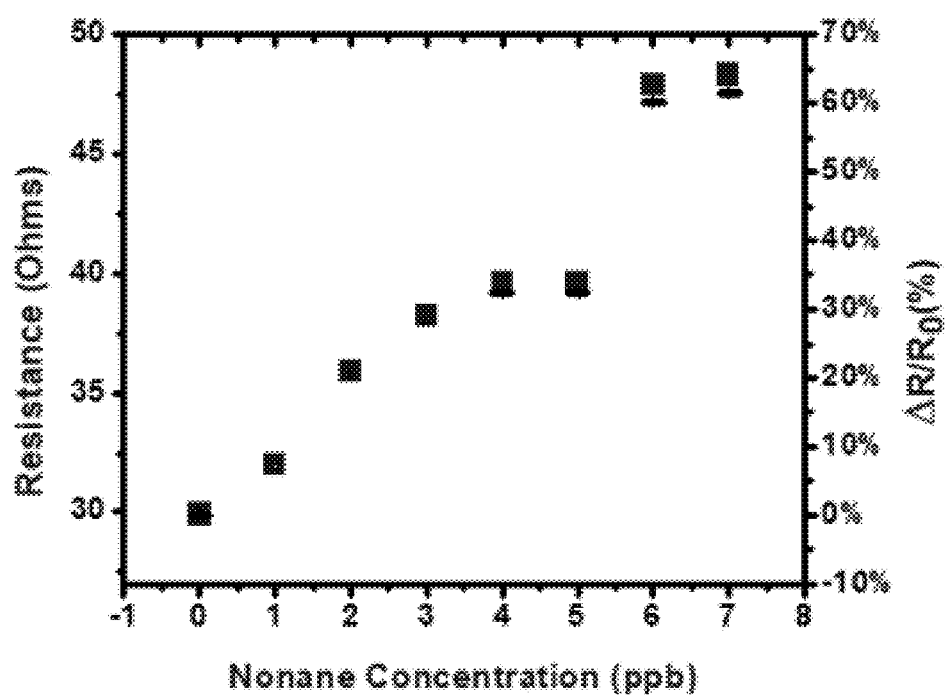
FIG. 15A is a graph of resistance and normalized resistance versus nonane concentration, and shows the response of the nonane sensor of Example 3 to varying concentrations of nonane.
Figures 15B, 15C:
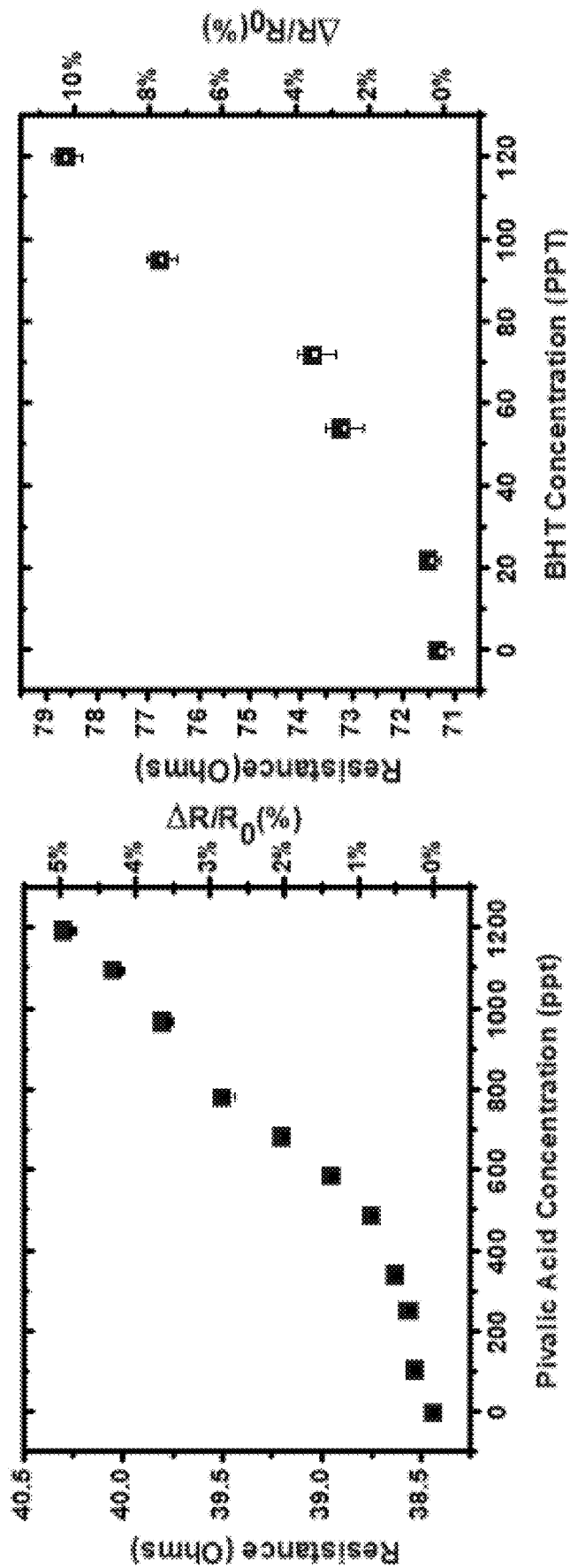
FIG. 15B is a graph of resistance and normalized resistance versus pivalic acid concentration, and shows the response of the pivalic acid sensor of Example 3 to varying concentrations of pivalic acid.
FIG. 15C is a graph of resistance and normalized resistance versus BHT concentration, and shows the response of the BHT sensor of Example 3 to varying concentrations of BHT.

FIG. 12 is a graph of resistance versus concentration, and shows the reaction of the sensor of Example 2 to varying concentrations of pivalic acid. The sensor was tested over the range of 1-80 ppb. For each measurement, a syringe of a specific vapor of pivalic acid was injected into the chamber, and it was left to reach equilibrium, while the resistance was monitored. The sensor shows a linear behavior over the tested range. Also, the high affinity between GR and PB led to increase the electron transfer between the layers.

Example 3. An Array of Electrochemical Gas Sensors to Detect Volatile Organic Compounds Biomarkers in the Exhaled Breath Abstract. Alzheimer's disease (AD) is a chronic neurodegenerative disease that destroys memory and other important mental functions. Reported herein is a fast, low-cost, completely non-invasive and quantitative method for early diagnosis of AD through sensing the biomarker volatile organic compounds (VOCs) in exhaled breath by using novel ultra-sensitive and highly selective electrochemical gas sensors. 24 biomarker VOCs have been identified in exhaled breath for AD, which exhibit statistically significant differences between AD patients and healthy controls by using gas chromatography-mass spectroscopy. The accuracy of diagnosis of these VOCs was determined to be 85% through different groups of AD patients. These VOCs are structurally very similar and found in low concentrations of less than 20 ppb. Each of the electrochemical sensors is only sensitive to one specific biomarker VOC, and not sensitive to the other VOCs or other components of the exhaled breath such as nitrogen, water, carbon dioxide, etc. The sensors have the size of $1 \times 5 \times 5$ mm$^3$ each. Therefore, ultra-sensitive and highly selective sensors are needed to detect these biomarker VOCs. The breath sensors have been demonstrated to show sensitivity of 20~100 part per trillion (ppt), high selectivity, and have shown excellent preliminary results on transgenic human APOE4 knock-in rats with AD, compared to healthy controls. Sensor of these teachings for detecting and recognizing target molecules includes a layer of molecularly imprinted polymer disposed on a thin layer of graphene-Prussian blue on silicon substrate. The silicon-based sensor has the potential to be used as an electronic device. This can be connected to a micro controller unit to monitor the resistance change and transmit the data to a smartphone through Bluetooth.

Introduction. Diagnosis from patient's breath odor dates back to ancient Greek. However, modern breath analysis started in the 1970s when Pauling first discovered the concept of the volatile organic compounds and determined more than 200 components in human breath using gas chromatography-mass spectroscopy. Clinical studies showed that ethane and pentane concentrations were elevated in inflammatory diseases. Acetone was linked to dextrose metabolism and lipolysis. Exhaled isoprene concentrations showed correlations with cholesterol biosynthesis and exhaled levels of sulfur-containing compounds were elevated in liver failure and allograft rejection. Looking at a set of volatile markers may enable recognition and diagnosis of complex diseases even neurodegenerative disease. Pathophysiological process of AD typically begins at least a decade before symptoms appear. Early and accurate diagnosis of AD could save 15% which is about $7.9 trillion in medical and care costs.

The NINCDS-ADRDA Alzheimer's Criteria proposed in 1984 by the National Institute of Neurological and Communicative Disorders and Stroke and the Alzheimer's Disease and Related Disorders Association are among the most used in diagnosis of AD, which were updated in 2011 to incorporate new findings on AD. The updated AD diagnostic guidelines propose staging of disease (preclinical, mild cognitive impairment (MCI), and Alzheimer's dementia), and potential use of biomarkers. While physicians can almost always determine if a person has dementia, it may be difficult to determine the exact cause. The diagnosis procedure starts with medical history review and physical examination. This will continue with neurological exams such as reflexes, coordination, muscle tone and strength, eye movement, speech, and sensation. Then the patient needs to go through mental status tests to evaluate memory, cognitive ability and mood disorder. The next step will be laboratory test and spinal tap (cerebrospinal fluid test) to check the biomarker of AD. The last step would be brain imaging such as MRI, CT, EEG, ECG and PET scan to visualize the brain tissue. The diagnosis of AD is time-consuming, expensive, invasive, and usually requires a lot of efforts. The invasive procedures involved in the diagnosis of AD are particularly difficult and tedious for older patients. The sooner the disease can be diagnosed, the better treatment options can be provided. Furthermore, recent progress provides evidences that dementia can be reversed if it is diagnosed at early stage.

A low-cost non-invasive method for sensing biomarkers of AD would be ideal for assisting the diagnosis process, or for early diagnosis of AD. 24 biomarker VOCs have been identified using gas chromatography and mass spectrometry analysis and shown statistically significant differences in the average abundance of these biomarker VOCs in the breath of AD, PD and healthy controls. The same group used sensors based on functionalized nanomaterials for sensing these AD biomarker VOCs and have demonstrated 85% accuracy to distinguish AD patients from healthy controls. However, these nanomaterials-based VOC sensors are qualitative only, not selective, and rely on pattern recognition for selectivity.

Demonstrated herein are three breath sensors with ppt sensitivity and high selectivity based on MIP/Graphene sensors inheriting ultra-high sensitivity of graphene.

Fabrication procedure. An electrochemical gas sensor with glassy carbon electrode as the substrate has been reported. Silicon was substituted by the glassy carbon because of its compatibility with electronic devices. A 380-micron thick, p-type silicon was used as the substrate. Silicon is a not conductive, so a thin layer of chromium was sputtered on the silicon substrate to improve the conductivity. A schematic of the sensors is depicted in FIG. 13A. The procedure of reducing graphene from graphene oxide and mixing with Prussian blue has been explained in Example 1. After the deposition of graphene-PB on Cr-coated silicon, a thin layer of molecularly imprinted polymer is formed through the cyclic voltammetry. The electrochemical polymerization procedure starts with mixing pyrrole with the template molecules (e.g., biomarker VOCs) in aqueous solution of phosphate buffer solution. The polymerization procedure starts with mixing pyrrole with the 0.5 mM of template molecule in aqueous solution of phosphate buffer solution. The cyclic voltammetry to deposit the polymer was carried out for 20 cycles with a scan rate of 50 mV/s, from −0.35 to +0.85 V vs. Ag/AgCl. An array of three sensors has been fabricated and tested, sensing butylated hydroxytoluene, pivalic acid (2,2-dimethylpropanoic acid) and nonane (4-methyl-octane). BHT is chosen from aromatic benzene-derived category and nonane from methylated alkane group from the biomarker VOCs. Pivalic acid was the smallest molecule among all the twenty-four chemicals.

Testing Results. A sealed chamber was fabricated for the testing procedures. All the sensors have been tested for sensitivity toward water vapor and nitrogen as well and it was concluded that the sensors are not sensitive to them. Pure $N_2$ or $H_2O$ has been pumped to the sealed chamber and the sensors' responses were monitored for 10 minutes. No changes in the resistance were observed, so it can be suggested that the sensors were not sensitive to nitrogen or water vapor. Each sensor was also tested toward a few structurally similar molecules to check their selectivity. The nonane sensor was tested with 5 ppm concentration of undecane ($C_{11}H_{24}$), dodecane ($C_{12}H_{26}$) and heptane ($C_7H_{16}$), and no resistance change was noticed over the 15 minutes. In a similar procedure, the pivalic acid sensor was tested with benzoic acid ($C_7H_6O_2$), and the BHT sensor was tested with styrene ($C_8H_8$), and it could be concluded that each sensor is just sensitive toward the specific targeted chemical molecule. For the solid templates such as BHT and pivalic acid, a specific amount of solid BHT was placed inside a syringe and left to evaporate. Then the vapor was injected to the chamber. The same procedure was done for pivalic acid. It is a solid template and testing was done over the range of 5-75 ppb of concentration. However, nonane was liquid and the least amount measured was 1 μl. The liquid was left inside a syringe to evaporate and the vapor was injected into the chamber, and the testing was done over the range of 1-10 ppb.

FIGS. 14A-15C show the test results. Clearly, these sensors show excellent selectivity, and ultra-high sensitivity of 1-100 ppt (part per trillion), which is 2-3 orders of magnitude better than other reported gas sensors.

Figure 16B:
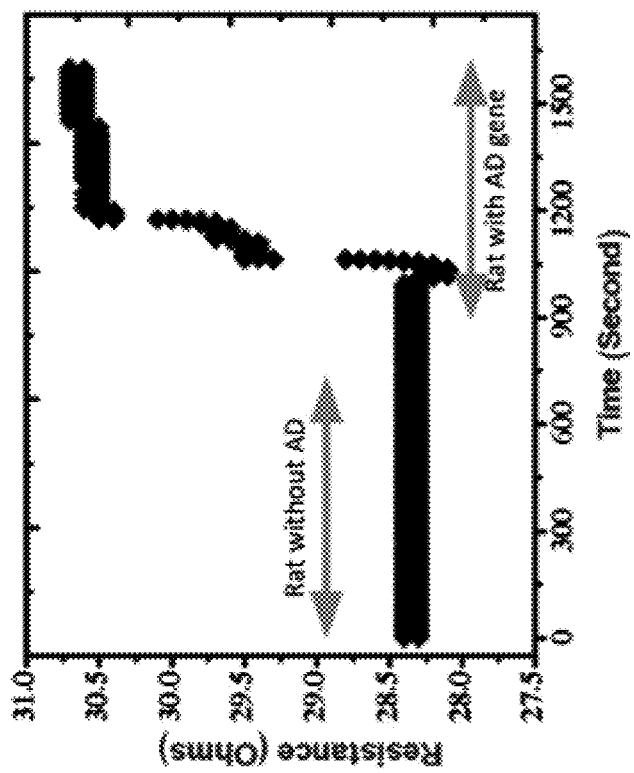
FIG. 16B is a graph of resistance versus time, and shows the results of rat testing described in Example 3 using the nonane sensor of Example 3.
Figure 16A:
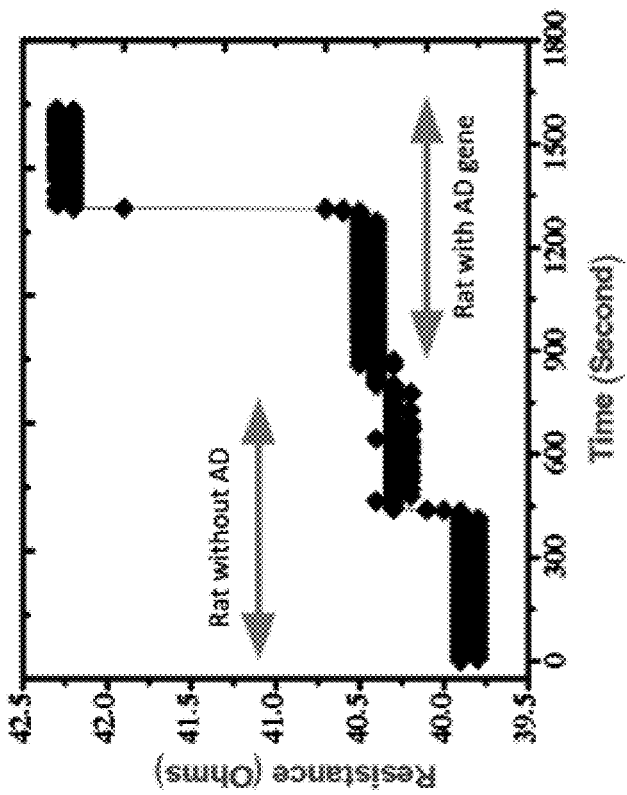
FIG. 16A is a graph of resistance versus time, and shows the results of rat testing described in Example 3 using the pivalic acid sensor of Example 3.

Animal Testing. Animal testing was conducted at Northeastern University Center for Translational Neuro-imaging. In this experiment, the sensors were tested toward AD rat and non-AD rat's breath. The two rats were on the same high sugar and high fat diet and at the same age, 18 months old. The only difference between the rats was the APOE4 gene, which is the AD gene. The APOE4 gene, present in approximately 10-15% of people, increases the risk for Alzheimer's and lowers the age of onset. Having one copy of E4 (E3/E4) can increase the risk of AD by 2 to 3 times, while two copies (E4/E4) can increase the risk by 12 times. All the testing procedures were done in a small chamber. The sensor was placed on the ceiling of the chamber while letting the rat breathe inside for 15 minutes. Pivalic acid and nonane sensors' results are shown in FIGS. 16A and 16B, respectively. The pivalic acid sensor did not react to the breath of non-AD rat while showing 2.3 Ohms resistance increase to the breath of AD rat. The nonane sensor resistance jumped for 0.4 Ohms during the experiment with non-AD rat, which could be because of contact problem or a little concentration of nonane in the breath print of healthy rat. The sensor later showed a 1.8 Ohms increase toward the testing of AD rat breath.

Conclusion. An array of three electrochemical gas sensors has been fabricated to sense BHT, pivalic acid and nonane in the air at ppb and ppt level of concentration. All these three chemicals were detected at a very low concentration, less than 20 ppb, the target range for sensing it in the exhaled breath of Alzheimer's patients. The developed electrochemical sensors exhibited excellent performance such as a low limit of detection, wide range of detection, high selectivity, good stability and easy reproducibility toward sensing these chemicals. This array of silicon-based sensors is capable to connect to a smartphone via Bluetooth, and transfer the data with a micro controller. A mobile application can be developed and connected to the array of sensors, which can show the graphical results to the users and can be applied toward early diagnosis of Alzheimer's disease through exhaled breath. Compared to other reported gas sensors, the proposed breath sensors have multifold advantages: (1) These sensors have ultra-high sensitivity, which can reach a detection limit of single-digit of parts per trillion (ppt) and are the most sensitive gas sensors ever reported. The ppt sensitivity enables early detection of biomarker VOCs, thus makes possible early diagnosis of AD; (2) Our proposed sensors are extremely selective; only respond to the template biomarker VOC molecules, not responsive to other VOCs, water vapor, carbon dioxide, or nitrogen, which are the main components of exhaled breath; and (3) The sensors are inexpensive, and have fast response in the order of a few seconds, thus enabling fast diagnosis of AD.

Example 4. Molecularly-Imprinted Gas Sensor for Detection of Lung Cancer Lung Cancer is the Leading Cancer Killer in Both Men and Women in the United States Nearly 226,000 people are diagnosed with lung cancer each year. The cost of lung cancer was $13.4 billion in 2015 based on a National Institutes of Health report. Lung cancer typically doesn't cause signs and symptoms in its earliest stages. Early diagnosis is the only factor that can improve survival rate in lung cancer. VOCs are organic chemicals with high vapor pressure (at room temperature), that, along with inert gases, form less than 1% of the exhaled breath. From the physiological point of view, the exchange of blood and the air in the alveolar leads to transferring chemicals in the blood, which was formed during metabolism inside the body, to find a way to the exhaled breath. Thus, the measurement of VOCs in the breath can provide a window into the biochemical processes of the body.

Figure 17A:
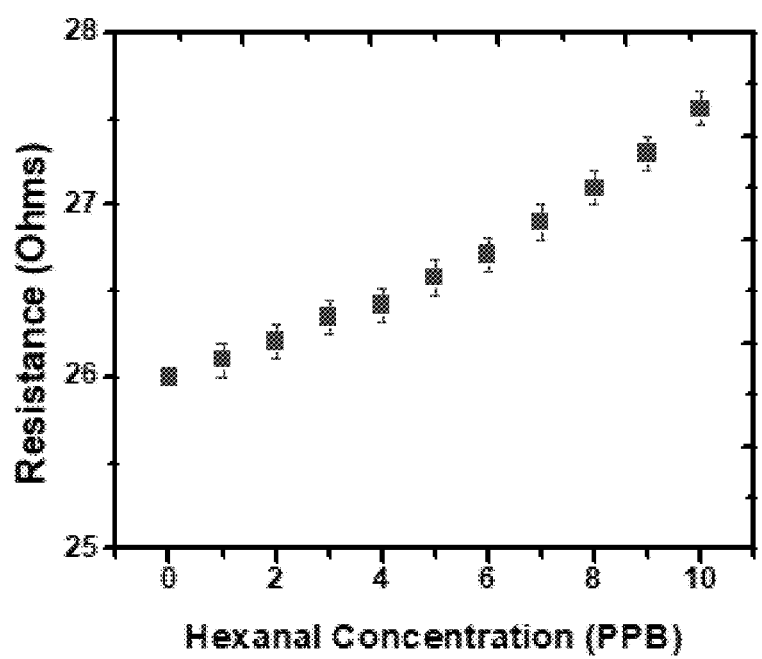
FIG. 17A is a graph of resistance versus hexanal concentration, and shows the response of the hexanal sensor of Example 4 to varying concentrations of hexanal.
Figure 17C:
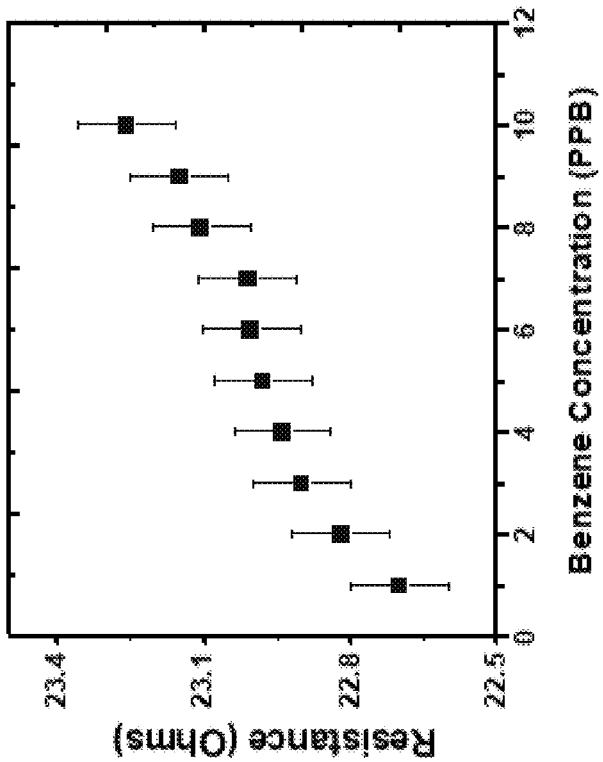
FIG. 17C is a graph of resistance versus benzene concentration, and shows the response of the benzene sensor of Example 4 to varying concentrations of benzene.
Figure 17B:
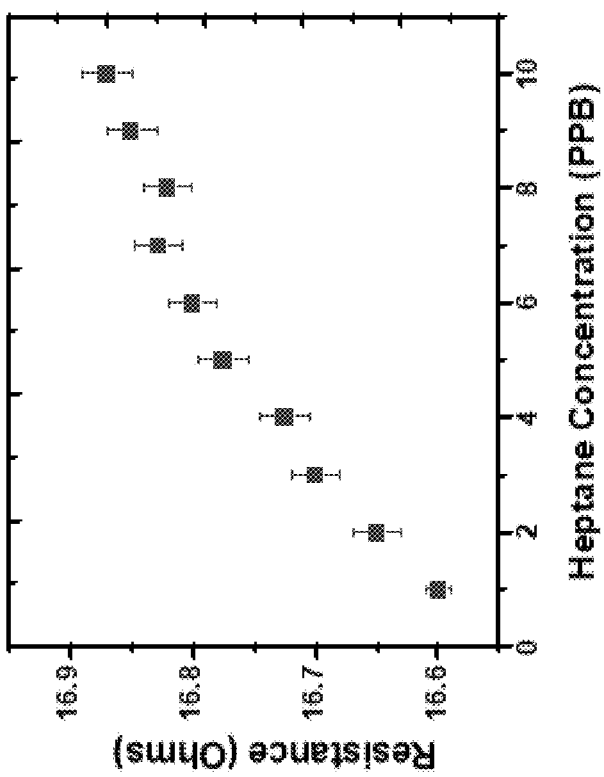
FIG. 17B is a graph of resistance versus heptane concentration, and shows the response of the heptane sensor of Example 4 to varying concentrations of heptane.

A new methodology is proposed herein to detect hexanal, benzene and heptane, which are three chemicals found in the breath print of lung cancer patients. Towards this end, three sensors selective for hexanal, benzene and heptane, respectively, were fabricated using the procedure disclosed in Example 3, except that 0.5 mM of each template (hexanal, benzene and heptane, respectively) was used during MIP polymerization. The testing results for the sensors are graphed in FIGS. 17A-17C.

These sensors are cost-effective, sense instantly, super sensitive at the level of the part per trillion and highly selective as they are sensitive only to their template molecules. These silicon-based sensors can be combined as an array and get connected with a smartphone through Bluetooth by using Raspberry-pi. The Raspberry-pi measures the resistance of each sensor and interprets the data with machine learning tools and transfers the data through Bluetooth to a smartphone. The success of this project will represent a completely new and game-changing approach to the diagnosis of diseases, which is quick, low-cost, non-invasive, and quantitative. Besides benefiting patients, these breath sensors will significantly benefit research scientists, physicians, clinicians, ultimately providing unprecedented opportunities for better understanding and curing the diseases.

Example 5. Molecularly Imprinted Gas Sensor for Early Diagnosis of Alzheimer's Disease Alzheimer's disease (AD) is a neurodegenerative brain disease and the most common form of dementia. It is characterized by a decline in memory, language, problem solving, reasoning, planning and other thinking and cognitive skills. Currently, an estimated 5.7 million Americans have AD, and the expenses on taking care of these AD patients amount to $277 billion in 2018. Pathophysiological process of AD typically begins decades before the symptoms appear. Early and accurate diagnosis of AD could lead to early intervention and treatment, which could save up to $7.9 trillion in medical and care costs. Recent discoveries show that AD can be prevented, and in many cases its associated cognitive decline can be reversed, if early diagnosis is realized. However, early diagnosis of AD has been challenging. Current diagnostic guidelines for AD are time-consuming, expensive, invasive, and usually requires memory clinics.

The biomarker VOCs in exhaled breath for AD have been recently identified. The accuracy of diagnosis of these VOCs was determined to be 85% through different groups of AD patients. These VOCs are structurally very similar and found in low concentrations of less than 20 ppb. Therefore, ultra-sensitive and highly selective gas sensors are needed to detect these VOCs. Disclosed herein are two sensors to detect biomarkers pivalic acid and nonane in the breath. The 24 biomarkers can be categorized into benzene derivative and methyl alkane chemicals. BHT was picked from benzene derivative category while nonane is from methylated alkane category. Pivalic acid is the smallest molecule among all the chemicals.

The fabrication process and the structure of the nonane the pivalic acid sensors are very similar to the BHT sensor of Example 1. The preparation of Graphene and Prussian blue is explained step by step in Example 1 herein. However, the preparation of the MIP for each sensor is different. The activation of GCE surface was modified by adding 2 mg of the GR-PB powder dissolved in 2 mL of DI water. It was stored overnight. A solution of 1 L phosphate buffer solution containing 0.5 mM of the template molecule (nonane or pivalic acid) and 6.937 mL of pyrrole was stirred for 2 h (pH 6.8, adjusted with $H_2SO_4$) to be used for cyclic voltammetry (CV). The cyclic voltammetry to deposit the polymer was carried out for 20 cycles with a scan rate of 50 mV/s, from −0.35 to +0.85 V vs. Ag/AgCl.

Figure 18B:
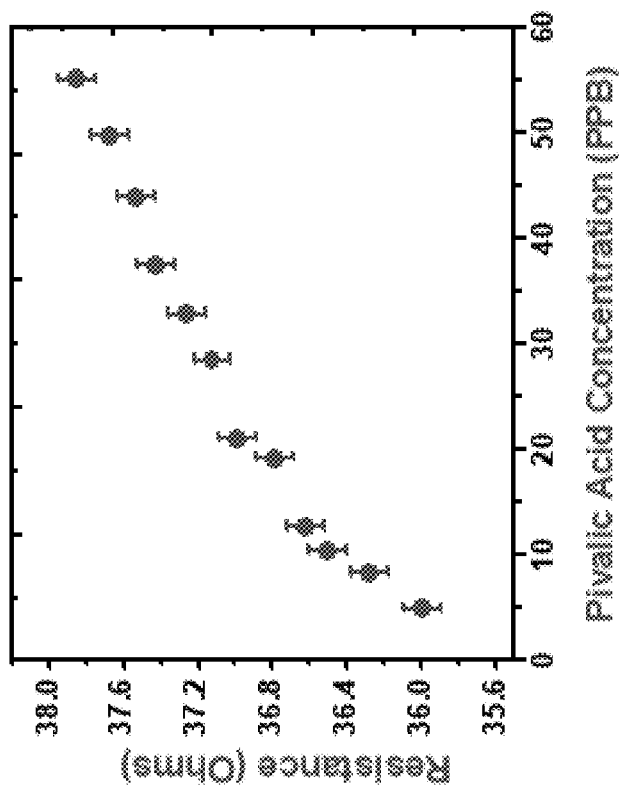
FIG. 18B is a graph of resistance versus pivalic acid concentration, and shows the response of the pivalic acid sensor of Example 5 to varying concentrations of pivalic acid.
Figure 18A:
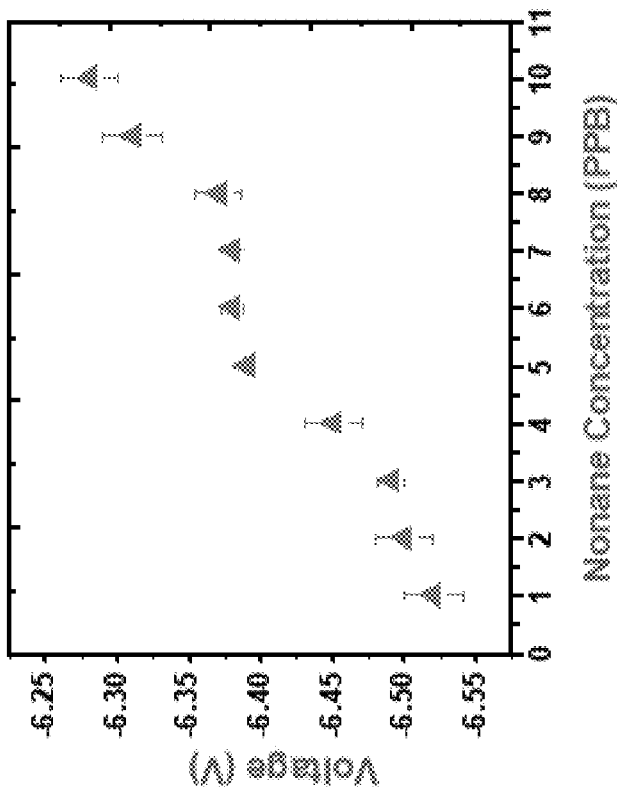
FIG. 18A is a graph of voltage versus nonane concentration, and shows the response of the nonane sensor of Example 5 to varying concentrations of nonane.

These two sensors were tested in a sealed chamber. The results are shown in FIGS. 18A and 18B. The nonane sensor was tested from 1 to 10 ppb of the concentration and the pivalic acid sensor was tested from 1 to 55 ppb of the concentration. Both the sensors are showing a linear behavior which later can be used to identify the concentration of the specific chemical from the measured resistance.

In this work, a novel array of sensitive and selective molecularly-imprinted electrochemical sensors for the detection of pivalic acid and nonane, which are the two biomarkers of the Alzheimer's disease in the exhaled breath, were constructed. The MIP film was electropolymerized on the surface of the GR-PB modified GCE. The GR-PB composites displayed perfect electrochemical properties and electron transfer for sensing in a very low concentration. The developed electrochemical sensors exhibited excellent performance such as a low limit of detection (20 parts per trillion), linear behavior, high selectivity and good stability toward the template molecules. These low-cost sensors can be used repeatedly after being washed with a proper solvent. Combination of these sensor might find a way toward early and non-invasive diagnosis of AD from the exhaled breath.

Example 6. Animal Testing

Figure 19:
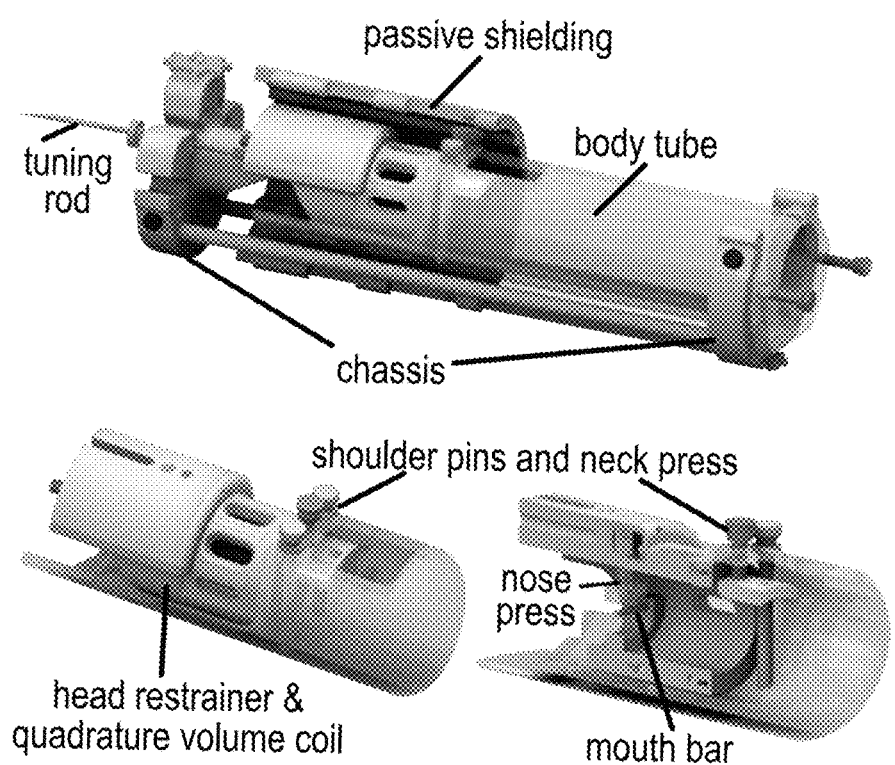
FIG. 19 is a depiction of the experimental set-up for the rat testing described in Example 6, and shows the apparatus used to restrain the rats during testing while keeping their mouths open.
Figure 20A:
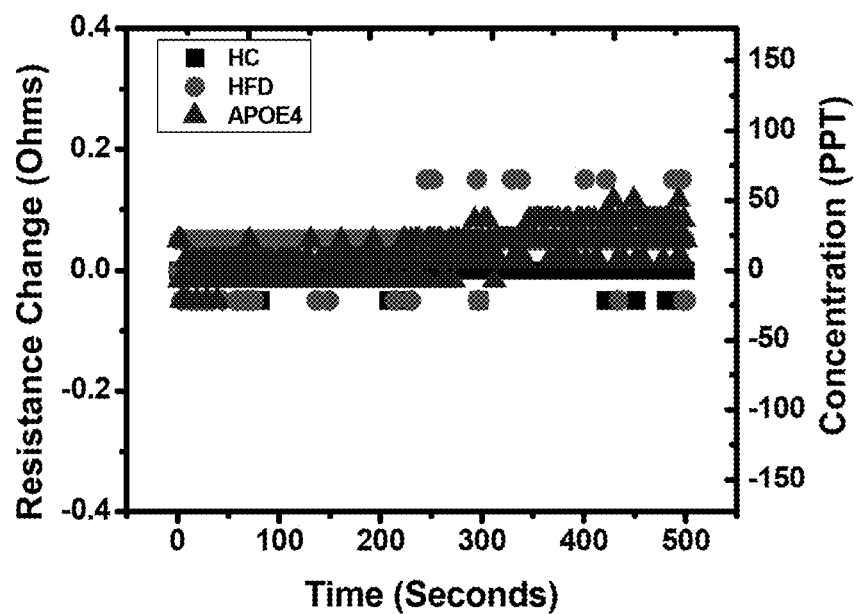
FIG. 20A is a graph of resistance versus time, and shows the response of a BHT sensor constructed in accordance with the BHT sensor described in Example 3 to the breath of female rats in the rat test described in Example 6.
Figure 20B:
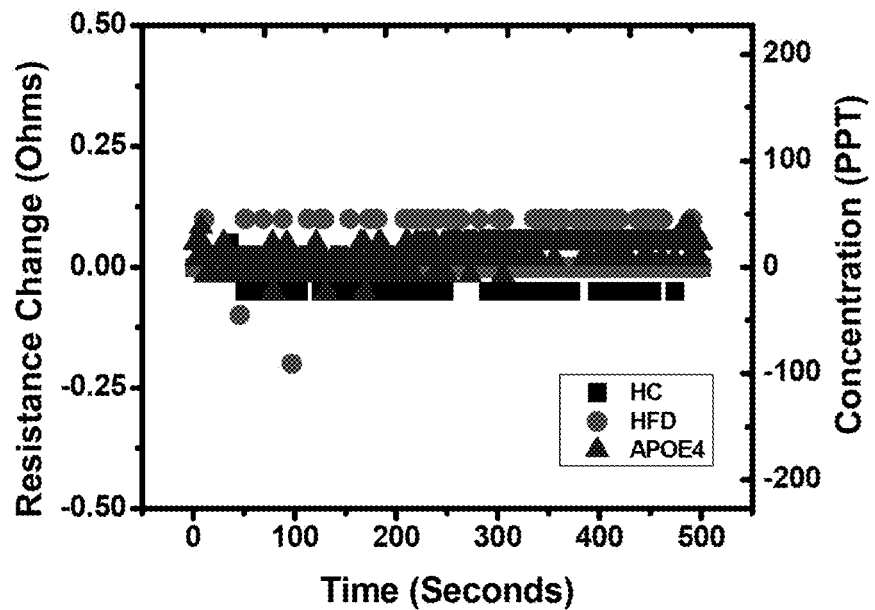
FIG. 20B is a graph of resistance versus time, and shows the response of a pivalic acid sensor constructed in accordance with the pivalic acid sensor described in Example 3 to the breath of female rats in the rat test described in Example 6.
Figure 20C:
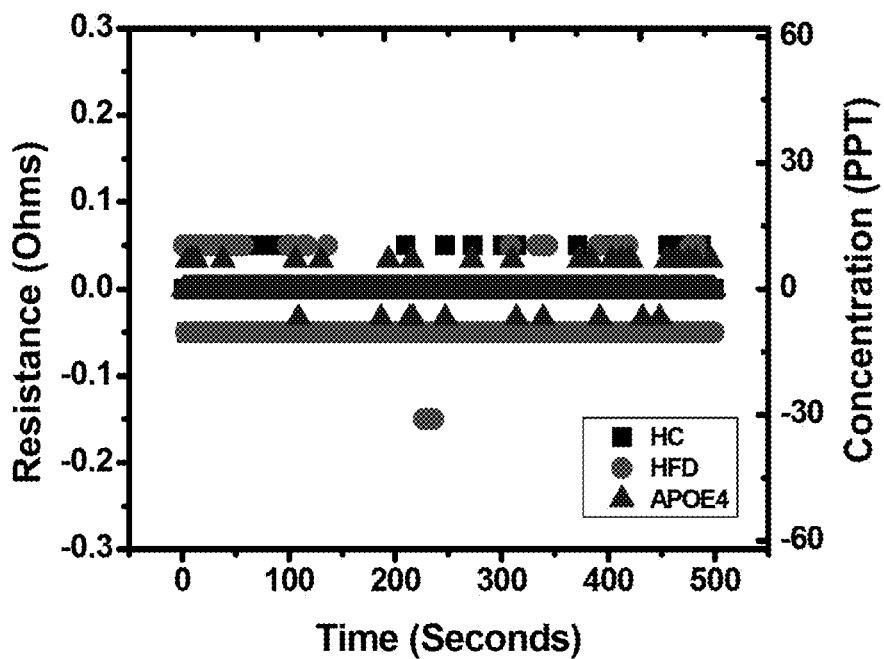
FIG. 20C is a graph of resistance versus time, and shows the response of a nonane sensor constructed in accordance with the nonane sensor described in Example 3 to the breath of female rats in the rat test described in Example 6.
Figure 20D:
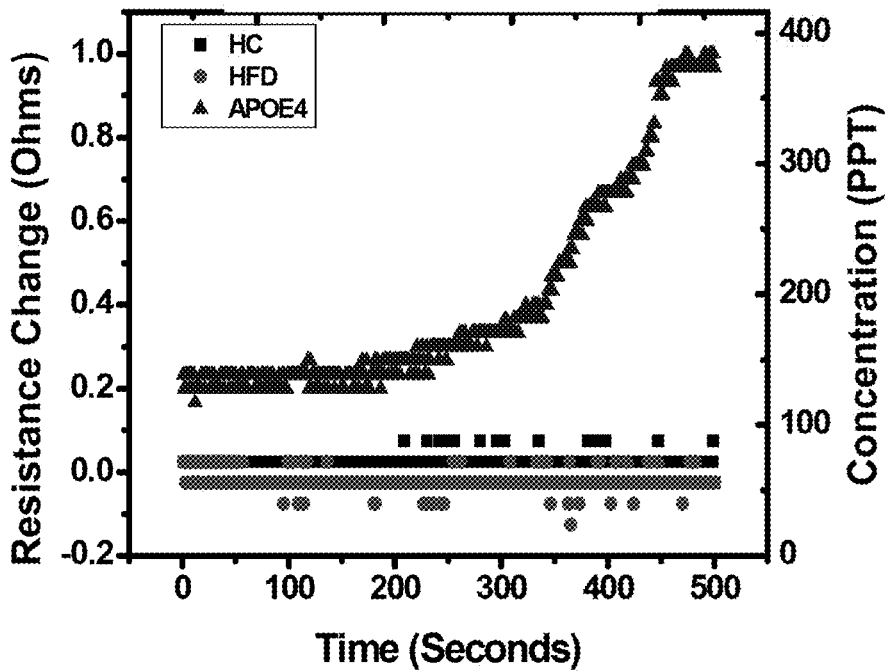
FIG. 20D is a graph of resistance versus time, and shows the response of a nonane sensor constructed in accordance with the nonane sensor described in Example 3 to the breath of male rats in the rat test described in Example 6.
Figure 20E:
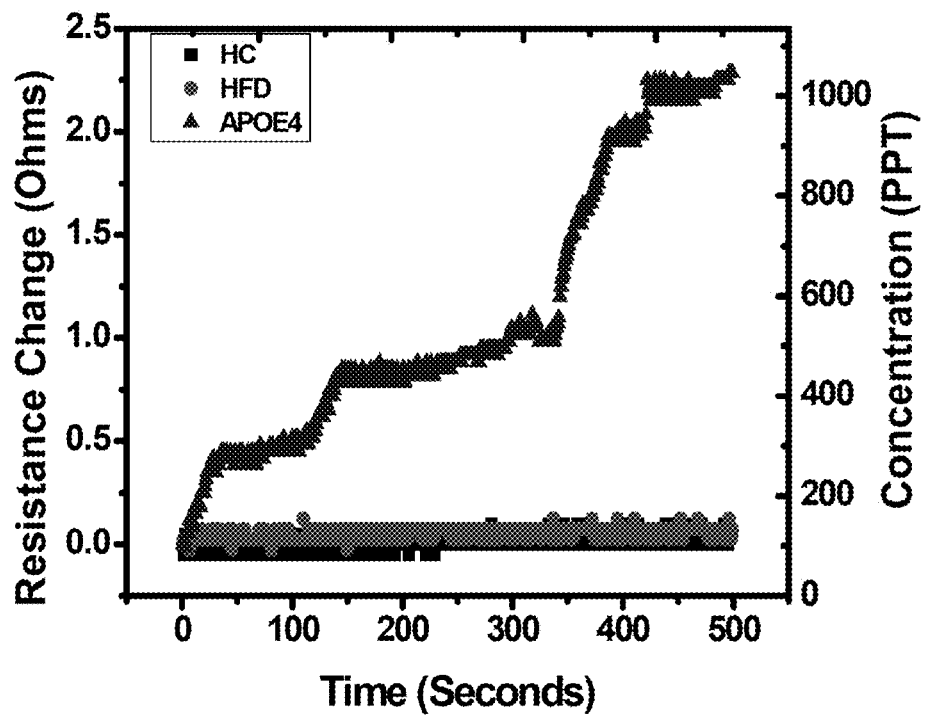
FIG. 20E is a graph of resistance versus time, and shows the response of a pivalic acid sensor constructed in accordance with the pivalic acid sensor described in Example 3 to the breath of male rats in the rat test described in Example 6.
Figure 20F:
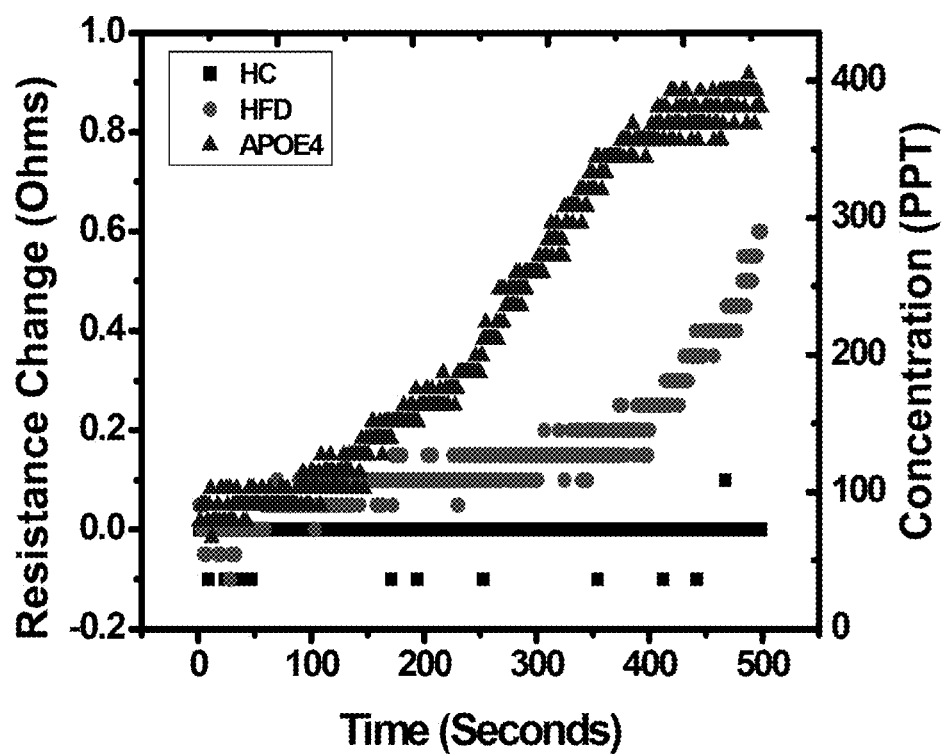
FIG. 20F is a graph of resistance versus time, and shows the response of a BHT sensor constructed in accordance with the BHT sensor described in Example 3 to the breath of male rats in the rat test described in Example 6.

All the animal testing was conducted at Northeastern University Center for Translational Neuro-imaging. Four sets of animals were tested: 4-month old healthy control (3 male), 15-month old on high fat-high sugar diet (1 female, 2 male), 15-month old with APOE4 gene on high fat-high sugar diet (3 male, 3 female). An apparatus was designed to restrain the rats during the experiment while keeping their mouth open. The apparatus is depicted in FIG. 19, and includes a body tube, head restrainer, shoulder pins and neck press, and nose press for confining and restraining the rats. The mouth bar maintained the rats' mouths in the open position. A chassis was used to provide support to the apparatus, and to maintain the various elements of the apparatus in a fixed position during the experiment to minimize motion artifact. The sensors were placed very closed to the rats' mouths so they could detect the chemicals exhaled by the rats. The design of the restraining system included a padded head support, obviating the need for ear bars and helping to reduce animal discomfort while minimizing motion artifact.

All animal work was performed in accordance with the approved animal protocols and Institutional Animal Care and Use Committee. Rats were housed in standard cages and maintained on a 12 hr light/dark cycle with ad libitum access to food and water. Routine health monitoring of the colony was performed at IDEXX (Columbia, Mo., USA) and revealed no evidence of infection with serious known pathogens.

The testing results of three sensors (BHT, Nonane and Pivalic acid) for 12 rats are depicted in FIGS. 20A-20F.

MRIs of the rats were also taken. The results, not shown, demonstrate that APOE male rats have less neuron connection in their brain compared to wild type male rats, which could be counted as a malfunction in the brain and memory loss. MRI results of the APOE female rats showed the opposite effect: the APOE gene helped the females to maintain healthier brains.

The breath results are completely compatible with the MRI results. None of the sensors responded to the healthy control rats, or the old rats on high fat diet. The sensors also did not detect the template molecules on the breath of female APOE rats. However, the sensors did react to the breath of male APOE rats. A resistance increase of 1-2.5 Ohms happened within 500 seconds of the experiment.

REFERENCES

1. Alzheimer's Association, 2016 Alzheimer's disease facts and figures. *Alzheimer's & Dementia* 2016, 12, 459-509.
2. De Meyer G; Shapiro F.; Vanderstichele H.; Diagnosis-independent Alzheimer disease biomarker signature in cognitively normal elderly people. *Arch. Neural,* 2010, 67(8), 949-956.
3. Selkoe, D. J.; Yamazaki, T.; Citron, M.; Podlisny, M. B.; Koo, E. H.; Teplow, D. B.; Haass, C. The role of APP processing and trafficking pathways in the formation of amyloid beta-protein. *Ann NY Acad. Sci.* 1996, 777, 57-64.
4. Iaccarino F. H.; Singer C. A.; Martorell J. A.; Rudenko A.; Gao F.; Gillingham Z. T.; Mathys, H.; Seo, J.; Kritskiy, O.; Abdurrob, F.; Adaikkan, C.; Canter, R. G.; Rueda, R.; Brown, E. N.; Boyden, E. S; Tsai, L.; Gamma frequency entrainment attenuates amyloid load and modifies microglia. *Nature* 2016, 540, 230-252.
5. Canter, R. G; Penney, J.; Tsai, L.; The road to restoring neutral circuits for the treatment of Alzheimer's disease. *Nature* 2016, 539.
6. Urraca, J. L.; Aureliano, C. S. A.; Schillinger, E.; Esselmann, H.; Wiltfang, Sellergren, B.; Polymeric complements to the Alzheimer's disease biomarker β-amyloid isoforms Aβ1-40 and Aβ1-42 for blood serum analysis under denaturing conditions, *Journal of the American chemical society* 2011, 133, 9220-9223.
7. Hu. W. I.; Chen-Plotkin, A.; Arnold, S. E.; Grossman, M.; Clark, C. M.; Shaw, L. M.; McCluskey, L.; Elman, L.; Karlawish, J.; Hurtig, H. I.; Siderowf, A.; Lee, V. M. Y.; Soares, H.; Trojanowski, J. Q.; Biomarker discovery for Alzheimer's disease, frontotemporal lobar degeneration, and Parkinson's disease. *Acta Neuropathol* 2010, 120, 385-399.
8. Bach, J. P.; Gold, M.; Mengel, D.; Hattesohl, A.; Lubbe, D.; Schmid, S.; Tackenberg, B.; Rieke, J.; Maddula, S.; Baumbach, J. I.; Nell, C.; Boeselt, T.; Michelis, J.; Judith Alferink, J.; Heneka, M.; Oertel, W.; Jessen, F.; Janciauskiene, S.; Vogelmeier, C.; Dodel, R.; Koczulla, A. R. Measuring Compounds in Exhaled Air to Detect Alzheimer's Disease and Parkinson's Disease, *Plos One* 2015, DOI: 10.1371,
9. Liguoril, C.; F.; Francesca Izzi, Nuccetelli, M.; Bernardini, S.; Sarpa, G. M.; Cum, F.; Marciani, M. G.; Mercuri, N. B.; Romigi, A.; Beta-amyloid and phosphorylated tau metabolism changes in narcolepsy over time. *Sleep Breath* 2016, 20, 277-283.
10. Buszewski, B.; Kesy, M.; Ligor, T.; Amann, A. Human exhaled air analytics: Biomarkers of diseases. *Biomed Chromatogr.* 2007, 21, 553-566.
11. Hibbard, T.; Killard, A. J. Breath ammonia analysis: Clinical application and measurement. Breath Ammon, Clin. App. Meas. 2011, 41, 21-35.
12, Schmidt, F. M.; Vaittinen, O.; Metsala, M.; Lehto, M.; Forsblom, C.; Groop, P. H.; Halonen, L. Ammonia in breath and emitted from skin. *J. Breath Res.* 2013, 7, 017109.
13. Broza, Y. Y.; Haick, H.; Nanomaterial-based sensors for detection of disease by volatile organic compounds. *Nanomedicine* 2013, 8(5), 785-797.
14. Nakhleh, M. K.; Amal, H.; Jeries, R.; Broza, Y. Y.; Aboud, Alaa Ghana, A.; Ivgi, H.; Khatib, S.; Badarneh, S.; Har-Shai, L.; Glass-Marmor, L.; Lejbkowicz, I.; Miller, A.; Badarny, S.; Winer, R.; Finberg, J.; Cohen-Kaminsky, S.; Perros, F.; Montani, D.; Girerd, B.; Garcia, G.; Simonneau, G.; Nakhoul, F.; Baram, S.; Salim, R.; Hakim, M.; Gruber, M.; Ronen, O.; Marshak, T.; Doweck, I.; Nativ, O.; Bahouth, Z.; Shi, D.; Zhang, W.; Hua, Q.; Pan, Y.; Tao, L.; Liu, H.; Karban, A.; Koifman, E.; Rainis, Skapars, R.; Sivins, A.; Ancans, G.; Liepniece-Karele, Kikuste, I.; Lasina, I.; Tolmanis, I.; Johnson, D.; S. Z.; Fulton, J.; Wells, J. W.; L. H.; Humbert, M.; Leja, M.; Peled, N.; H. Diagnosis and Classification of 17 Diseases from 1404 Subjects via Pattern Analysis of Exhaled Molecules. *ACS Nano* 2017, 11 (1), 112-125.
15. Pokorskide, M.; Sartuccib, F.; Domenicib, L.; Giulioa, C. D. Volatile organic compounds (VOCs) fingerprint of Alzheimer's disease! Andrea Mazzatentaa. *Respiratory Physiology & Neurobiology* 2015, 209, 81-84.
16. Glassy carbon electrodes Characterization and electrochemical activation, Dekanskia, A.; Stevanovic, J.; Stevanovic, R.; Nikolic, B. Z.; Jovanovic, V. M.; 16. Carbon 39 (2001) 1195-1205
17. Van der Linden, W. F.; Dicker, J. W.; Glassy carbon as electrode material in electro-analytical chemistry, Anal Chim Acta 1980; 119:1-24.
18. Schedin, F.; Geim, A. K.; Morozov, S. V.; E. W.; Blake, P.; Katsnelson, M. I.; Novoselov, K. S.; Detection of individual gas molecules adsorbed on grapheme. *Nat. Mater.* 2007, 6, 652-655, doi:http://dx.doi.org/10.1038/nmat1967. 17660825.
19. Alizadeh, T.; Hamedsoltani, L. Graphene/graphite/molecularly imprinted polymer nanocomposite as the highly selective gas sensor for nitrobenzene vapor recognition. *Journal of Environmental Chemical Engineering* 2014, 2, 1514-1526
20. Zhao, J.; Chen, G.; Zhu, L.; Li, G. Graphene quantum dots-based platform for the fabrication of electrochemical biosensors. *Electrochem. Commun.* 2011, 13, 31-33,
21. Li, J; Jiang, Y; Zhai, Y; Liu, H; Li, L. Prussian Blue/Reduced Grapheme Oxide Composite for the Amperometric Determination of Dopamine and Hydrogen Peroxide. *Analytical Letters* 2015, 48:17, 2786-2798, DOI: 10.1080/00032719.2015.1052141
22. Li, Y. X.; Li, Y. J.; Mei, H.; Bin, Q.; Lin, Z. Y.; Lin, Z. A.; Cai Z. W.; Chen, G. N. *Biosens. Bioelectron* 2013, 42, 612-617.
23. Cui, M.; Liu, S.; Lian, W.; Li, J.; Xua, W.; Huang. A molecularly-imprinted electrochemical sensor based on a graphene-Prussian blue composite-modified glassy carbon electrode for the detection of butylated hydroxyanisole in foodstuffs. *J. Analyst* 2013, 138, 5949.
24. Janiak, D. S.; Kofinas, P. Molecular imprinting of peptides and proteins in aqueous media. *Anal Bioanal Chem* 2007, 389, 399-404.
25. Algieri, C.; Drioli, E.; Guzzo, L. Donato, L. Bio-Mimetic Sensors Based on Molecularly Imprinted *Membranes. Sensors (Basel).* 2014, 14(8), 13863-13912.
26. Vasapollo, G.; Del Sole, R.; Mergola, L.; Lazzoi, M. R.; Scardino, A.; Scorrano, S.; Mele, G. Molecularly Imprinted Polymers: Present and Future Prospective. *Int J Mol Sci.* 2011, 12(9), 5908-5945.
27. Dickert, F. L.; Leiberzeit, P.; Miarecha, S. G.; Mann, K. J.; Hayden, O.; Palfinger, C.; Synthetic receptors for chemical sensors-subnano- and micrometer patterning by imprinting techniques, *J of Biosensors and Bioelectronics.* 2004, 20, 1040-1044.
28. Chen, X.; Cao, M.; Li, Y.; Hu, W.; Wang, P.; Ying, K.; Hongming Pan, H. A study of an electronic nose for detection of lung cancer based on a virtual SAW gas sensors array and imaging recognition Method, *J of Meas. Sci. Technol.* 2005, 16, 1535-1546.
29. Capuano, R.; Santonico, M.; Pennazza, G.; Ghezzi, S.; Martinelli, E.; Roscioni, C.; Lucantoni, G.; Galluccio, G.; Paolesse, R.; Di Natale, C.; D'Amico, A.; The lung cancer breath signature: a comparative analysis of exhaled breath and air sampled from inside the lungs, *Nature Scientific Report.* 2015, 1-10, DOE 383 10.1038/srep 16491.
30. Ma, Y; Siitonen, A; Chemical sensor using molecularly-imprinted single layer graphene, patent no: US 20160377611 A1, 2016.
31. Hummers W. S., Offeman, R. E. Preparation of graphene oxide, *J. Am. Chem. Soc.* 1958, 80, 1339.
32. Stankovich, S.; Dikin, D. A.; Piner, R. D., Kohlhaas, K. A., Kleinhammes, A.; Jia, Y.; Wu. Y.; Nguyen, S. T.; Ruoff, R. S. Synthesis of graphene-based nanosheets via chemical reduction of exfoliated graphite oxide. *Carbon* 2007, 45, 1558-1565.
33. Park, S.; An, J.; Potts J. R.; Velamakanni, A.; Murali, S.; Ruoff, R. S. Hydrazine-reduction of graphite- and graphene oxide, *Carbon* 2011, 49, 3019-3023.
34. Pei, S.; Cheng, H. The reduction of graphene oxide, *Carbon* 2011, 1-19.
35. Zhang, M.; Hou, C.; Halder, A.; Ulstrup, J.; Chi, Q. Interlocked graphene-Prussian blue hybrid composites enable multifunctional electrochemical applications. *Biosensors and Bioelectronics* 2017, 89, 570-577.
36. Jin, E.; Lu, X.; Cui, L.; Chao, D.; Wang, C. Fabrication of graphene/prussian blue composite nanosheets and their electrocatalytic reduction of $H_2O_2$, *Electrochimica Acta* 2010, 55, 7230-7234.
37. A Ping, J. F.; Wu, J.; Fan K.; Ying, Y. B. An amperometric sensor based on Prussian blue and poly(o-phenylenediamine) modified glassy carbon electrode for the determination of hydrogen peroxide in beverages, *Food Chem.* 2011, 126, 2005-2009.
38. Tisch, U., Schlesinger, I., Ionescu, R., Nassar, M., Axelrod, N., Robertman, D., Tessler, Y., Azar, F., Marmur, A., Aharon-Peretz J., Haick, H., (2013). "Detection of Alzheimer's and Parkinson's disease from exhaled breath using nanomaterial-based sensors" *J Nanomedicine* 8(1): 43-56.
39. Peng, G., Tisch, U., Haick, H., (2009). "Detection of Nonpolar Molecules by Means of Carrier Scattering in Random Networks of Carbon Nanotubes: Toward Diagnosis of Diseases via Breath Samples", *Nanoletters,* 9(4): 1362-1368.
40. Kleisiaris, C. F., Sfakianakis, C., Papathanasiou, I. V., (2014). "Health care practices in ancient Greece: The Hippocratic ideal", *J Med Ethics Hist Med,* 7 (6): 1-5
41. Pauling, L., Robinson, A. B., Teranishi, R., et al. (1971). "Quantitative analysis of urine vapor and breath by gas-liquid partition chromatography", *Proc Natl Acad Sci,* 68:2374-6.
42. Annette G. Dent, A. G., Sutedja, T. G., Zimmerman, P. V., (2013). "Exhaled breath analysis for lung cancer", *J Thorac Dis.,* 5 (Suppl 5):540-550.
43. De Meyer, G., Shapiro, F., Vanderstichele, H., (2010). "Diagnosis-independent Alzheimer disease biomarker signature in cognitively normal elderly people". *J Arch. Neurol.* 67(8): 949-956.
44. 2018 Alzheimer's disease facts and figures, Alzheimer's association, (2018). 1-88.
45. McKhann, G M., Knopman, D S., Chertkow, H., Hyman, B T., Jack, C R Jr., Kawas, C H., Klunk, W E., Koroshetz, W J., Manly, J J., Mayeux, R., Mohs, R C., Morris, J C., Rossor, M N., Scheltens, P., Carrillo, M C., Thies, B., Weintraub, S., Phelps, C H., (2011). "The diagnosis of dementia due to Alzheimer's disease: recommendations from the National Institute on Aging-Alzheimer's Association workgroups on diagnostic guidelines for Alzheimer's disease."*Alzheimers Dement.* 7(3): 263-9.
46. Bredesen, D., (2017). "The End of Alzheimer's: The First Program to Prevent and Reverse Cognitive Decline", Penguin publisher: 1-320.
47. Bredesen, D., (2014). "Reversal of cognitive decline: A novel therapeutic program" *J of Aging* 6(9): 707-717.
48. Sherzai, A., Sherzai, T., (2017). "The Alzheimer's Solution: A Breakthrough Program to Prevent and Reverse the Symptoms of Cognitive Decline at Every Age" Harper Collins publisher, 1-228.
49. Gunther, E C., Smith, L V., Kostylev, M A., Naderi, Z K., Supattapone, S., Strittmatter, S M., (2019). "Rescue of Transgenic Alzheimer's Pathophysiology by Polymeric Cellular Prion Protein Antagonists" *J Cell Reports* 26:145-158.
50. Dumurgier, J., Hanseeuw, B J., Hatling, F B., Judge, K A., Schults, A P., et al Gomez-Isla, T., (2017). "Alzheimer's Biomarker and Future Decline in Cognitive Normal Older Adults" *J Alzheimers Dis* 60(4): 1451-1459.
51. Nakamura, A., Kaneko, N., Villemagne, V L., Kato, T., Doecke, et al. Yanagisawa, K., (2018). "High performance plasma amyloid-β biomarkers for Alzheimer's disease" *Nature* 554: 249-273.
52. Katsnelson, M I., Novoselov. K S., (2007). "Graphene: new bridge between condensed matter physics and quantum electrodynamic," *J of Solid State Commun.* 143: 3-13.
53. Hwang, E H., Adam, S., Sarma. D S., (2007). "Transport in chemically doped graphene in the presence of adsorbed molecules". *Phys. Rev. B* 76:195-421.
54. Lin, C Y., Tai, D F., Wu. T Z., (2003). "Discrimination of Peptides by Using a Molecularly Imprinted Piezoelectric Biosensor" *Chem. Eur. J.* 9: 5107-5110.
55. Cui, M., Liu, S., Lian, W., Li, J., Xua, W., Huang. A., (2013). Molecularly-Imprinted Electrochemical Sensor Based on a Graphene-Prussian blue Composite-Modified Glassy *Carbon* Electrode for the Detection of Butylated Hydroxyanisole in Foodstuffs" *J. Analyst* 138: 5949-5955.
56. Michaelson, D. M., (2014). "APOE epsilon4: the most prevalent yet understudied risk factor for Alzheimer's disease" *Alzheimers Dement,* 10(6): 861-868.
57. Tisch, U., Schlesinger, I., Ionescu, R., Nassar, M., Axelrod, N., Robertman, D., Tessler, Y., Azar, F., Marmur, A., Aharon-Peretz J., Haick, H., (2013). "Detection of Alzheimer's and Parkinson's disease from exhaled breath using nanomaterial-based sensors" *J Nanomedicine* 8(1): 43-56.
58. Emam, S., Adedoyin, A., Geng, X., Zaeimbashi, M., Adams, J., Ekenseair, A., Podlaha-Murphy, E., Sun N. X., (2018). "A Molecularly-Imprinted Electrochemical Gas Sensor to Sense Butylated Hydroxytoluene in Air" *J of Sensors* 2018: 1-9.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of detecting one or more analytes associated with a disease or condition in a subject suspected to have the disease or condition, or at risk for developing the disease or condition, comprising:
measuring the resistance of a device that has been or is in contact with a sample obtained from the subject, the device comprising:
one or more layers of metal on a layer of silicon; and
a layer of molecularly imprinted polymer that is selective for the one or more analytes associated with the disease or condition in electrical communication with the one or more layers of metal; and
one or more electrical contacts, wherein the one or more electrical contacts are in electrical communication with the layer of molecularly imprinted polymer,
wherein: the one or more layers of metal are each independently selected from a layer of chromium, platinum, gold, nickel, cobalt, tungsten, rhodium, iridium, silver, tin, titanium or tantalum, or an alloy thereof, and are not electrical contacts; and the device has an inherent resistance, and a difference between the inherent resistance of the device and the resistance of the device contacted with the sample indicates one or more analytes associated with the disease or condition have been detected.

2. The method of claim 1, wherein the disease or condition is Alzheimer's disease.
3. The method of claim 1, wherein the one or more analytes are nonane, pivalic acid or butylated hydroxy toluene, or a combination of any of the foregoing.
4. The method of claim 1, wherein the disease or condition is lung cancer.
5. The method of claim 1, wherein the one or more analytes are hexanal, heptane or benzene, or a combination of any of the foregoing.
6. The method of claim 1, wherein the resistance of the device is measured while the device is in contact with the sample.
7. The method of claim 1, wherein the sample is the subject's exhaled breath.
8. The method of claim 1, wherein the metal is chromium.
9. The method of claim 1, wherein the one or more layers of metal is from about 10 microns to about 20 microns thick.
10. The method of claim 1, wherein the layer of silicon is from about 250 microns to about 650 microns thick.
11. The method of claim 1, wherein the layer of molecularly imprinted polymer is from about 5 nanometers to about 500 nanometers thick.
12. The method of claim 1, wherein the inherent resistance of the device is from about 1 ohm to about 100 ohms.
13. The method of claim 1, wherein the device further comprises one or more layers of graphene between the one or more layers of metal and the layer of molecularly imprinted polymer, the one or more layers of graphene being in electrical communication with the one or more layers of metal and the layer of molecularly imprinted polymer.
14. The method of claim 13, wherein the one more layers of graphene comprise potassium ferrocyanide.
15. The method of claim 13, wherein the one or more layers of graphene comprise from about one to about 50 layers of graphene.
16. The method of claim 1, wherein the molecularly imprinted polymer is derived from pyrrole.
17. The method of claim 1, wherein the molecularly imprinted polymer is selective for the one or more analytes in gas form.
18. The method of claim 1, wherein the one or more analytes are volatile organic compounds.
19. A method of diagnosing a disease or condition in a subject suspected to have the disease or condition, or at risk for developing the disease or condition, comprising: measuring the resistance of a device that has been or is in contact with a sample obtained from the subject, the device comprising:
one or more layers of metal on a layer of silicon; and
a layer of molecularly imprinted polymer that is selective for the one or more analytes associated with the disease or condition in electrical communication with the one or more layers of metal; and
one or more electrical contacts, wherein the one or more electrical contacts are in electrical communication with the layer of molecularly imprinted polymer,
wherein: the one or more layers of metal are each independently selected from a layer of chromium, platinum, gold, nickel, cobalt, tungsten, rhodium, iridium, silver, tin, titanium or tantalum, or an alloy thereof, and are not electrical contacts; and the device has an inherent resistance, and a difference between the inherent resistance of the device and the resistance of the device contacted with the sample indicates the subject has the disease or condition.

* * * * *

UNITED STATES PATENT AND TRADEMARK OFFICE
CERTIFICATE OF CORRECTION

PATENT NO. : 11,701,031 B2
APPLICATION NO. : 17/453941
DATED : July 18, 2023
INVENTOR(S) : Nian Xiang Sun, Shadi Emam and Adam Keith Ekenseair It is certified that error appears in the above-identified patent and that said Letters Patent is hereby corrected as shown below:

In the Claims

In Claim 19, Column 32, Line 51, delete "for the one" and insert -- for one --.

Signed and Sealed this
Twenty-ninth Day of August, 2023

Katherine Kelly Vidal
*Director of the United States Patent and Trademark Office*